「(12) United States Patent
Pomara

(10) Patent No.: US 7,709,208 B2
(45) Date of Patent: May 4, 2010

(54) METHODS FOR DIAGNOSIS OF MAJOR DEPRESSIVE DISORDER

(75) Inventor: Nunzio Pomara, Rye Brook, NY (US)

(73) Assignee: New York University, New York, NY (US)

(*) Notice: Subject to any disclaimer, the term of this patent is extended or adjusted under 35 U.S.C. 154(b) by 0 days.

(21) Appl. No.: 11/269,857

(22) Filed: Nov. 8, 2005

(65) Prior Publication Data

US 2006/0105394 A1 May 18, 2006

Related U.S. Application Data

(60) Provisional application No. 60/625,824, filed on Nov. 8, 2004.

(51) Int. Cl.
G01N 33/53 (2006.01)
G01N 33/567 (2006.01)
G01N 33/543 (2006.01)
G01N 33/566 (2006.01)

(52) U.S. Cl. .................. 435/7.1; 435/7.21; 435/7.9; 435/7.92; 435/7.94; 436/501

(58) Field of Classification Search .............. None
See application file for complete search history.

(56) References Cited

U.S. PATENT DOCUMENTS 5,593,846 A * 1/1997 Schenk et al. ............. 435/7.9

OTHER PUBLICATIONS

DSM-IV, APA, Fourth Edition, 2005, pp. 133-136 and 138-139.*
van Gool et al. Neurosci. Lett., 1994, vol. 172, pp. 122-124.*
Green et al., Arch. Neurol, 2003, vol. 60, pp. 753-759.*
Pomara, et al, Neurochem Res, 31, 341-349 (2006).
Lewczuk, et al., Neurobiology of Aging, 25, 273-281 (2004).
Mayeux, et al., Neurology, 61, 1185-1190 (2003).
Mayeux, et al., Ann. Neurol., 46, 412-416 (1999).

* cited by examiner

Primary Examiner—Olga N Chernyshev
(74) Attorney, Agent, or Firm—Klauber & Jackson, LLC

(57) ABSTRACT

The present invention relates to methods of diagnosing, prognosing or treating diseases or disorders in which elevated levels of Abeta protein, including $abeta_{1-42}$ are prevalent. In particular, the present invention relates to methods of diagnosing, prognosing or treating a major or minor depressive episode/disorder attributed to elevated levels of Abeta protein, including $abeta_{1-42}$, found particularly in body fluids including whole blood, blood cells, serum, plasma, urine and CSF. The invention also relates to the treatment of these disorders by administering an agent that either prevents production of Abeta, prevents aggregation of Abeta fibrils, or that increases the degradation or clearance of Abeta. In addition, the invention provides a method of treating or preventing a major or minor depressive disorder comprising administering an agent that prevents or interferes with Abeta-induced neurotoxicity. The present invention also relates to pharmaceutical compositions comprising such agents and methods of screening for novel agents.

7 Claims, 7 Drawing Sheets

Schematic structure of the amyloid β-protein precursor (APP)

```
                              10                                                    20
Asp – Ala – Glu – Phe – Arg – His – Asp – Ser – Gly – Tyr – Glu – Val – His – His – Gln – Lys – Leu – Val – Phe – Phe –

Ala – Glu – Asp – Val – Gly – Ser – Asn – Lys – Gly – Ala – Ile – Ile – Gly – Leu – Met – Bal – Gly – Gly – Val – Val – Ile – Ala
                              30                                        39    40    41    42
```

FIG. 7

METHODS FOR DIAGNOSIS OF MAJOR DEPRESSIVE DISORDER

CROSS-REFERENCE TO RELATED APPLICATIONS

The present application is a non-provisional application claiming the priority of copending provisional application Ser. No. 60/625,824, filed Nov. 8, 2004, the disclosure of which is incorporated by reference herein in its entirety. Applicants claim the benefits of this application under 35 U.S.C. §119(e).

FIELD OF THE INVENTION

The present invention relates to the identification of enhanced levels of amyloid beta protein, for example, $Abeta_{1-42}$, in subjects suffering from a major depressive disorder and to the role of amyloid beta protein in the onset and development of this disorder, and to the use of amyloid beta protein and/or the genes encoding the same for e.g., clinical screening, diagnosis, prognosis, therapy and prophylaxis, as well as for drug screening and drug development in the treatment of a major depressive disorder.

BACKGROUND

In the majority of major depressive disorders, little is known about a link between changes at the cellular or molecular level and nervous system structure and function. The paucity of detectable neurologic defects distinguishes major depressive disorders from neurological disorders where manifestations of anatomical and biochemical changes have been identified. Thus, the identification and characterization of cellular or molecular causative defects is desirable for improved treatment of major depressive disorders.

Depressive disorders come in different forms. A major depressive episode is manifested by a combination of symptoms that interfere with the ability to work, study, sleep, eat, and enjoy once pleasurable activities. The DSM-IV diagnostic criteria can be found in Tables I, II and III. Such a disabling episode of depression may occur only once but more commonly occurs several times in a lifetime. A minor depressive disorder is characterized by one or more periods of depressive symptoms that are identical to those found in major depression in duration, but which involve fewer symptoms and less impairment. Dysthymic disorder is a less serious form of depression and involves long-term, chronic symptoms that do not disable, but keep one from functioning well or from feeling good. Many people with dysthymia also experience major depressive episodes at some time in their lives. Bipolar disorder, also called manic-depressive illness is not nearly as prevalent as other forms of depressive disorders and is characterized by cycling mood changes, including severe highs (mania) and lows (depression).

Some types of depression appear to have a genetic component associated with their occurrence, suggesting that a biological vulnerability can be inherited. This appears to be the case with bipolar disorder. Furthermore, major depression seems to occur generation after generation. However, it can also occur in people who have no family history of depression.

Major depressive disorder is prevalent in a large number of elderly patients, resulting in a significant increase in the number of suicides in this population. The risk factors for late-life depression include female gender, unmarried status, having stressful life events and lack of a social support network.

Major depressive disorder is characterized by any of a number of symptoms, including persistent sadness or anxiety, or feelings of emptiness, hopelessness, pessimism, guilt, worthlessness, or helplessness. There may also be a loss of interest or pleasure in hobbies and activities that were once enjoyed. Individuals with major depressive disorder may also experience decreased energy, or fatigue, or may have difficulty concentrating, remembering, or making decisions. They may also experience insomnia, early-morning awakening, or oversleeping, appetite and/or weight loss or overeating and weight gain. They may have thoughts of death or suicide and suicide attempts. They may also experience restlessness, irritability, and may exhibit persistent physical symptoms that do not respond to treatment, such as headaches, digestive disorders, and chronic pain.

Major mood disorders are also associated with many other deleterious health related effects and the costs with disability and premature death represent an economic burden of $43 billion annually in the United States alone. Rates of depression co-occurring with other medical conditions are as follows: myocardial infarction: 20-40%, Parkinson's disease: 40%, Alzheimer's disease: 30-35%, stroke: 25-50%, cancer: 3-50%, HIV/AIDS: 10-20%, rheumatoid arthritis: 12%, diabetes mellitus: 14-18%, chronic pain: 30%, disabling tinnitus: 60%, end-stage renal disease: 5-22% and spinal cord injury: 37% (Goldman et al. J Gen Intern Med 1999, 14, 569-580; Wyatt and Henter 1995, Soc Psychiatry Psychiatr Epidemiolm 30, 213-219). Despite the devastating impact of these disorders on the lives of millions, there is still uncertainty about the differential diagnosis of depression in the presence of these disorders (Goldman et al. 1999, J Gen Med 14, 569-80; Schatzberg 1998, J Clin Psychiatry, 59, suppl 6:5-12; Goodwin and Jamison, 1990 Manic-depressive illness, New York, Oxford University Press).

Current therapies can be categorized into the following major classes of agents: mood stabilizers: lithium, divalproex, carbamazepine, lamotrigine; antidepressants: tricyclic antidepressants (eg. Desipramine, chlorimipramine, nortriptyline), selective serotonin reuptake inhibitors (SSRIs including fluoxetine (Prozac), sertraltrine (Zoloft), paroxetine (Paxil), fluvoxamine (Luvox), and citalopram (Celexa)), MAOIs, bupropion (Wellbutrin), venlafaxine (Effexor), and mirtazapine (Remeron); and atypical antipsychotic agents: Clozapine, Olanzapine, Risperidone. However, the cellular and molecular basis for the efficacy of currently used mood-stabilizing and mortality-lowering agents remains to be fully elucidated (Manji et al. 1999, J Clin Psychiatry, 60, 27-39). A significant number of patients respond poorly to existing therapies such as lithium, while many others are helped but continue to suffer significant morbidity (Chou 1991, J Clin Psychopharmacol 11, 3-21). The recognition of the significant morbidity and mortality of the severe mood disorders, as well as the growing appreciation that a significant percentage of patients respond poorly to existing treatments, has made the task of developing new therapeutic agents that work quickly, potently, specifically, and with fewer side effects one of major public health importance (Bebchuk et al. Arch Gen Psychiatry 2000 57, 95-7).

Hence it would be highly desirable to measure a substance or substances in samples of whole blood, blood cells, serum, plasma, urine or cerebrospinal fluid (CSF) that would lead to a positive diagnosis of a major depressive disorder or that would help to predict whether an individual is prone to developing such disorder. For example, the identification of proteins and/or the nucleic acids encoding proteins that are associated with the onset and progression of a major depressive disorder would be desirable for the effective diagnosis, prognosis and treatment of afflicted individuals. Appropriate steps may then be taken to treat early on with existing therapies. Alternatively, if one could demonstrate an association between a certain substance, such as a protein, in the blood of a depressed individual, it may be possible to utilize this information to develop new modes of therapy to prevent or treat such depressive disorders.

Given that the CSF bathes the brain, changes in its protein composition may reveal alterations in CNS protein expression pattern causatively or diagnostically linked to the disease. Alternatively, if reasonable amounts of proteins associated with the major depressive disorder are secreted or released into body fluids by diseased tissue in the living patient at the onset and/or during progression of the disease, such information may be utilized for early diagnosis and expedite a treatment strategy. In many cases these alterations will be independent of the genetic makeup of the individual and rather directly related to a set of molecular and cellular alterations that contribute to the pathogenic phenotype.

Therefore, a need exists to identify sensitive and specific biomarkers for the diagnosis of major and minor depressive disorders and to assess a subject's risk for developing such disorders. There is also a need for a biomarker to assess the severity and to predict the outcome of a major or minor depressive disorder in living subjects or to assess whether a particular therapy is efficacious in treating a subject having such disorders. More importantly, the need exists for identification of a biomarker substance that may be found in a body fluid that can be obtained with minimally invasiveness procedures for early and specific diagnosis of a major depressive disorder. Additionally, there is a clear need for new therapeutic agents for major depressive disorders that work quickly, potently, specifically, and with fewer side effects.

Accordingly, the methods provided herein address this need. The citation of references herein shall not be construed as an admission that such is prior art to the present invention.

SUMMARY OF THE INVENTION

In its broadest aspect, the present invention relates to methods of screening, diagnosis or prognosis of a major or minor depressive disorder in a subject. The invention further relates to identifying a subject at risk for developing a major or minor depressive disorder or for monitoring the effect of therapy administered to a subject suffering from a major or minor depressive disorder. More particularly, the methods of the invention are based on the previously unidentified finding of an increase in plasma levels of amyloid beta protein (in particular, $Abeta_{1-42}$) in elderly individuals suffering from a major depressive disorder. The invention further relates to methods of screening a subject for elevated levels of this protein in bodily fluids, in particular blood and/or plasma and/or urine, as a means of determining whether that subject has, or is prone to developing, a major depressive disorder. This protein may also be used as a means of assessing the effectiveness of therapy in subjects being treated for a major depressive disorder. Thus, such procedure for screening or diagnosing subjects with such conditions is viewed as a minimally invasive procedure that allows for rapid and sensitive screening. Furthermore, the association of elevated levels of Abeta protein or fragments thereof, such as $Abeta_{1-42}$, with depressive disorders and the possibility that such elevated levels of Abeta protein or fragments thereof, such as $Abeta_{1-42}$ may be a causative agent for development of such depressive disorders, allows for the identification and development of potential new therapeutic regimens directed towards lowering the levels of Abeta proteins or fragments thereof for treating such depressive disorders. In addition, although an elevation in $Abeta_{1-40}$ was not observed in the depressed patients in the study presented herein, it is still possible that because $Abeta_{1-40}$ is known to be neurotoxic (like $Abeta_{1-42}$), lowering the levels of both $Abeta_{1-42}$ as well as, $Abeta_{1-40}$ may be beneficial in treating depressive disorders and depressive symptoms. It is thus proposed that it may be necessary to lower the levels of Abeta proteins or peptide fragments, such as $Abeta_{1-40}$ and $Abeta_{1-42}$ to a level that poses no risk for development of depressive disorders or symptoms. The invention further relates to pharmaceutical compositions containing an agent that reduces brain amyloid beta levels, particularly $Abeta_{1-42}$, which may be achieved by such agent acting to prevent the production or generation of amyloid beta, by preventing the aggregation of amyloid beta, by increasing the degradation of amyloid beta, by increasing the clearance of amyloid beta from the brain, by preventing the neurotoxicity associated with abeta or by facilitating central and peripheral metabolism and clearance of amyloid beta. The invention also relates to screening methods that aid in the identification of novel agents that function through any one of the above-noted mechanisms for use in the treatment of a major or minor depressive disorder. The invention also relates to the inhibition of formation of potentially neurotoxic oligomeric forms of Abeta, especially $Abeta_{1-42}$.

Accordingly, a first aspect of the invention provides a method of screening, diagnosis or prognosis of a major or minor depressive disorder in a subject, said method comprising:
  a) collecting a biological test sample from said subject;
  b) analyzing said test sample for the presence of amyloid beta levels; and
  c) comparing the level of amyloid beta in the test sample with the level of amyloid beta in one or more persons free from a major or minor depressive disorder, or with a previously determined reference range for amyloid beta established from subjects free of a major or minor depressive disorder.

In another particular embodiment, the methods are used to identify a subject at risk for developing a major or minor depressive disorder, or for monitoring the effect of therapy administered to a subject having a major or minor depressive disorder. In yet another particular embodiment, the test sample is selected from the group consisting of whole blood, blood cells, serum, plasma, urine and CSF. In yet another particular embodiment, an elevation of amyloid beta in a subject correlates with the presence of a major depressive disorder. In yet another particular embodiment, the Abeta is $Abeta_{1-42}$. In yet another particular embodiment, the Abeta is a neurotoxic amount of $Abeta_{1-40}$. In yet another particular embodiment, the measurement of amyloid beta comprises a quantitative method selected from the group consisting of an immunological or biochemical assay specific for amyloid beta. In yet another particular embodiment, the method for measurement of amyloid beta is selected from the group consisting of an enzyme-linked immunosorbent assay (ELISA), a Western blot assay, a Northern blot assay, and a Southern blot assay. In another particular embodiment, the amyloid beta is amyloid $beta_{1-40}$ ($Abeta_{40}$) or amyloid $beta_{1-42}$ ($Abeta_{42}$) or fragments thereof.

In yet another particular embodiment, the quantitative method comprises testing at least one aliquot of the test sample, comprising the steps of:
  a. contacting/incubating the aliquot with an antibody that is immunospecific for amyloid beta;
  b. quantitatively measuring any binding that has occurred between the antibody and the test sample.

In yet another particular embodiment, the antibody is a monoclonal or polyclonal antibody specific for amyloid beta, in particular, amyloid beta$_{1-40}$ or amyloid beta$_{1-42}$. In yet another particular embodiment, the step of quantitatively measuring comprises testing a plurality of aliquots with a plurality of antibodies for the quantitative detection of amyloid beta.

A second aspect of the invention provides a method of treating and/or preventing a major depressive disorder comprising administering a therapeutically effective amount of an agent that reduces intracellular and/or extracellular amyloid beta levels in the brain and/or the circulation. In addition, the invention provides a method of treating or preventing a major depressive disorder comprising administering an agent that prevents or interferes with Abeta-induced neurotoxicity.

In a particular embodiment, the reducing of amyloid beta level is achieved by a method selected from the group consisting of preventing the production or generation of amyloid beta, or by preventing the aggregation of amyloid beta fibrils and deposition in cerebral parenchymal tissues and blood vessels, or by preventing the formation of oligomeric forms of Abeta, Abeta 1-40 or 1-42, or by increasing the degradation of amyloid beta, by increasing the clearance of amyloid beta from the brain, and by facilitating the central and/or peripheral metabolism and clearance of amyloid beta. In a particular embodiment, the amyloid beta is amyloid beta$_{1-40}$ or amyloid beta$_{1-42}$ or fragments thereof. In another particular embodiment, the reduction in amyloid beta levels results in reduced neurotoxicity.

In certain embodiments of the present invention, the administration of an agent/compound that reduces brain amyloid beta can be used in combination therapy with at least one other (a second) therapeutic agent. In a preferred embodiment, a composition comprising an agent/compound that reduces brain amyloid beta is administered concurrently with the administration of a second therapeutic agent, which can be part of the same composition as or in a different composition from that comprising the agent/compound that reduces brain amyloid beta including oligomeric forms of this peptide. In another embodiment, a composition comprising a compound that reduces brain amyloid beta is administered prior or subsequent to administration of a second therapeutic agent. As many of the disorders for which the compounds of the invention are useful in treating are chronic, in one embodiment combination therapy involves alternating between administering a composition comprising a compound that reduces brain amyloid beta and a composition comprising a second therapeutic agent, e.g., to minimize the toxicity associated with a particular drug. The duration of administration of the agent/compound that reduces brain amyloid beta or and/or second therapeutic agent can be, e.g., one month, three months, six months, a year, or for more extended periods, or on an alternate or intermittent schedule. In certain embodiments, when a compound that reduces brain amyloid beta is administered concurrently with a second therapeutic agent that potentially produces adverse side effects including, but not limited to, toxicity, the second therapeutic agent can advantageously be administered at a dose that falls below the threshold at which the adverse side is elicited. In another particular embodiment, the second drug that is used is effective at treating a major depressive disorder. In yet another particular embodiment, the second drug is administered concurrently, prior to, or after the agent that reduces brain amyloid beta levels. In yet another particular embodiment, the second drug is selected from the group consisting of Selective Serotonin Reuptake Inhibitors (SSRI), tricyclic antidepressants, and monoamine oxidase (MAO) inhibitors. In a more particular embodiment, the Selective Serotonin Reuptake Inhibitor is selected from the group consisting of citalopram, escitalopram HBr, fluvoxamine, paroxetine, fluoxetine, and sertraline. In a more particular embodiment, the tricyclic antidepressant is selected from the group consisting of amitriptyline, desipramine, doxepin, protriptyline, trimipramine and nortriptyline. In a more particular embodiment, the monoamine oxidase inhibitor is selected from the group consisting of phenelzine and tranylcypromine. In a more particular embodiment the second drug is selected from the group consisting of drugs that act as inhibitors of neuronal reuptake of both serotonin (5-HT) and norepinephrine (NE). In a more particular embodiment, the inhibitor of neuronal reuptake of both serotonin and norepinephrine is venlafaxine and duloxetine.

In another particular embodiment, the method further comprises treating with an agent that may interfere with the neurotoxic effects of amyloid beta on neurons or other brain cells, or on synaptic connections, which could lead to the development of, or may contribute to, the pathophysiology of a major depressive disorder in humans.

A third aspect of the invention provides a pharmaceutical composition for the treatment of a major depressive disorder. The pharmaceutical composition comprises an agent that prevents the production or generation of amyloid beta and a pharmaceutically acceptable carrier, or an agent that prevents aggregation of amyloid beta fibrils and deposition in cerebral parenchymal tissues and blood vessels, or by preventing the formation of oligomeric forms of Abeta, Abeta 1-40 or 1-42, or an agent that increases the degradation of amyloid beta and a pharmaceutically acceptable carrier, or an agent that increases the clearance of amyloid beta from the brain and a pharmaceutically acceptable carrier, or an agent that facilitates the metabolism of amyloid beta and a pharmaceutically acceptable carrier. The pharmaceutical composition is formulated for delivery by a route selected from the group consisting of intravenous, intramuscular, oral, subcutaneous, intrathecal, intracranial and intraventricular. In a particular embodiment, the amyloid beta is amyloid beta$_{1-40}$ or amyloid beta$_{1-42}$.

A fourth aspect of the invention provides a method of identifying a subject at risk for developing a major or a minor depressive disorder, said method comprising:
  a) collecting a test sample from said subject;
  b) analyzing said test sample for the presence of amyloid beta levels; and
  c) comparing the level of amyloid beta in the test sample with the level of amyloid beta in one or more persons free from a major or a minor depressive disorder, or with a previously determined reference range for amyloid beta established from subjects free of a major or a minor depressive disorder.

In a particular embodiment, the amyloid beta is amyloid beta$_{1-40}$ or amyloid beta$_{1-42}$ or fragments thereof. In another particular embodiment, the test sample is selected from the group consisting of whole blood, blood cells, serum, plasma, urine and cerebrospinal fluid (CSF).

A fifth aspect of the invention provides a diagnostic test for assessing a subject's risk of developing or having a major depressive disorder in a subject in which abnormal levels of amyloid beta are associated with the major depressive disorder, or for establishing a response to therapy for said condition, said diagnostic test comprising the following steps:
  a) collecting one tissue or cellular sample from said subject;
  b) measuring the level of amyloid beta in said one tissue or cellular sample and comparing the levels of amyloid beta with a range of predetermined values for amyloid beta, said values having been determined as falling within a reference range of amyloid beta, and wherein said level of amyloid beta is evaluated in conjunction with other risk factors for said major depressive disorder, said evaluation then being used to determine the subject's risk profile for said major depressive disorder; wherein said comparing provides information for assessing a subject's risk of developing or having a major depressive disorder in which abnormal levels of amyloid beta are associated with said major depressive disorder, or for establishing a prognosis for response to therapy for said condition, if the values of amyloid beta obtained from said one tissue or cellular sample fall outside of the normal range of amyloid beta, and if the level of amyloid beta correlates with the presence of one or more risk factors for said major depressive disorder.

In a particular embodiment, the amyloid beta is amyloid beta$_{1-40}$ or amyloid beta$_{1-42}$ or fragments thereof. In another particular embodiment, the test sample is selected from the group consisting of whole blood, blood cells, serum, plasma, urine and CSF.

A sixth aspect of the invention provides a method of measuring the effectiveness of a pharmaceutical composition comprising an agent for treating a subject having a major depressive disorder, comprising the steps of:
  a) determining the level of amyloid beta in a biological test sample obtained from the subject;
  b) administering an amount of a pharmaceutical composition comprising said agent to the patient;
  c) repeating step a) using a subsequently-collected biological sample obtained from the subject;
  d) comparing the level of amyloid beta determined in step a) with the level of amyloid beta determined in step c), wherein the effectiveness of the pharmaceutical composition is monitored by detecting a decrease in the level of amyloid beta in the subsequently-collected biological sample compared with the biological sample from step a).

In a particular embodiment, the amyloid beta is amyloid beta$_{1-40}$ or amyloid beta$_{1-42}$ or fragments thereof. In another particular embodiment, the test sample is selected from the group consisting of whole blood, blood cells, serum, urine, CSF and plasma.

A seventh aspect of the invention provides screening for agents that inhibit the production or generation of Abeta, or inhibit/prevent the aggregation of amyloid beta fibrils and deposition in cerebral parenchymal tissues and blood vessels, or by preventing the formation of oligomeric forms of Abeta, Abeta$_{1-40}$ or Abeta$_{1-42}$ or blocking their effect, or enhance the degradation or clearance of Abeta comprising the steps of:
  a) combining amyloid beta protein with an antibody specific for amyloid beta protein in a first sample;
  b) combining a test agent, amyloid beta protein and an antibody specific for amyloid beta protein in a second sample;
  c) comparing the difference in binding to amyloid beta between the two samples; and
  wherein a change or difference in binding to amyloid beta between the two samples indicates the presence of a test agent capable of binding to amyloid beta.

In one embodiment the method further comprises assessing a change in amyloid beta structure to determine any conformational/structural changes or changes in aggregation e.g. formation of amyloid beta fibrils. Methods for determining these changes are known to one skilled in the art and encompass standard biochemical and/or immunochemical assays. In another particular embodiment, the amyloid beta is Abeta$_{40}$, Abeta$_{42}$, or fragments thereof.

BRIEF DESCRIPTION OF THE DRAWINGS

FIG. 7 shows the amino acid sequence of beta amyloid beta peptides (Aβ$_{1-39}$, Aβ$_{1-40}$, and Aβ$_{1-42}$)(SEQ ID NO: 8).

DETAILED DESCRIPTION

Figure 1:
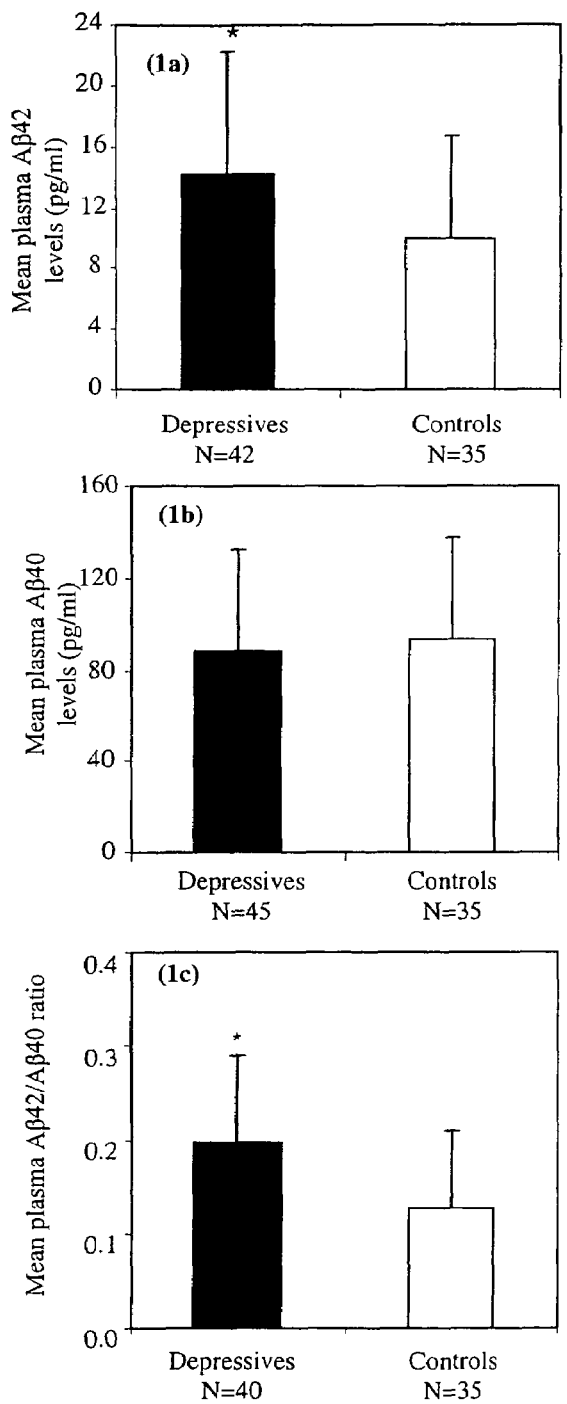
FIG. 1. Mean plasma Aβ$_{42}$ levels (1a), Aβ$_{40}$ levels (1b), and Aβ$_{42}$/Aβ$_{40}$ ratio (1c) in elderly depressives and controls. Error bars represent standard deviations.

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference in their entirety.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. PHames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

DEFINITIONS

The terms used herein have the meanings recognized and known to those of skill in the art, however, for convenience and completeness, particular terms and their meanings are set forth below.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to prevent, and preferably reduce by at least about 25 percent, more preferably by at least 50 percent, most preferably by at least 90 percent, a clinically significant change in a feature of pathology such as for example, elevated blood pressure, fever, or white cell count, as may attend its presence and activity. As related to the present invention, the term may also mean an amount sufficient to ameliorate or reverse one or more symptoms associated with the depressive order being treated. In particular, a "therapeutically effective amount" of the treatment may result in amelioration, reduction or elimination of at least one of the following symptoms: persistent sadness or anxiety, feelings of emptiness, hopelessness, pessimism, guilt, worthlessness, helplessness, a loss of interest or pleasure in hobbies and activities that were once enjoyed, decreased energy, or fatigue, difficulty concentrating, remembering, or making decisions, insomnia, early-morning awakening, or oversleeping, appetite and/or weight loss or overeating and weight gain, thoughts of death or suicide and suicide attempts, restlessness, irritability, and persistent physical symptoms that do not respond to treatment, such as headaches, digestive disorders, and chronic pain.

"Treatment" or "treating" refers to therapy, prevention and prophylaxis and particularly refers to the administration of medicine or the performance of medical procedures with respect to a patient, for either prophylaxis (prevention) or to cure or reduce the extent of or likelihood of occurrence of the infirmity or malady or condition or event in the instance where the patient is afflicted.

"Subject" or "patient" refers to a mammal, preferably a human, in need of treatment for a condition, disorder or disease.

An "antibody" is any immunoglobulin, including antibodies and fragments thereof, that binds a specific epitope. Such an antibody that binds a specific epitope is said to be "immunospecific". The term encompasses "polyclonal", "monoclonal", and "chimeric" antibodies, the last mentioned described in further detail in U.S. Pat. Nos. 4,816,397 and 4,816,567. Commonly used carriers that are chemically coupled to peptides include bovine or chicken serum albumin, thyroglobulin, and other carriers known to those skilled in the art. The coupled peptide is then used to immunize the animal (e.g, a mouse, rat or rabbit). The "chimeric antibody" refers to a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816,397.). The antibody may be a human or a humanized antibody. The antibody may be a single chain antibody. (See, e.g., Curiel et al., U.S. Pat. No. 5,910,486 and U.S. Pat. No. 6,028,059). The antibody may be prepared in, but not limited to, mice, rats, rabbits, goats, sheep, swine, dogs, cats, or horses. As used herein, the term "single-chain antibody" refers to a polypeptide comprising a $V_H$ region and a $V_L$ region in polypeptide linkage, generally linked via a spacer peptide (e.g., [Gly-Gly-Gly-Gly-Ser]$_x$), and which may comprise additional amino acid sequences at the amino- and/or carboxy-termini. For example, a single-chain antibody may comprise a tether segment for linking to the encoding polynucleotide. As an example, a scFv (single chain fragment variable) is a single-chain antibody. Single-chain antibodies are generally proteins consisting of one or more polypeptide segments of at least 10 contiguous amino acids substantially encoded by genes of the immunoglobulin superfamily (e.g., see The Immunoglobulin Gene Superfamily, A. F. Williams and A. N. Barclay, in Immunoglobulin Genes, T. Honjo, F. W. Alt, and T. H. Rabbitts, eds., (1989) Academic Press: San Diego, Calif., pp. 361-387, which is incorporated herein by reference), most frequently encoded by a rodent, non-human primate, avian, porcine, bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and, F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

"Agent" refers to all materials that may be used to prepare pharmaceutical and diagnostic compositions, or that may be compounds, nucleic acids, polypeptides, fragments, isoforms, variants, or other materials that may be used independently for such purposes, all in accordance with the present invention.

"Screening" or "Diagnosis" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

The essential features of a "major depressive episode" or "major depression" is a period of at least 2 weeks during which there is either a depressed mood or the loss of interest or pleasure in nearly all activities. The individual must also experience at least four additional symptoms drawn from a list that includes changes in appetite or weight, sleep, and psychomotor activity; decreased energy; feelings of worthlessness or guilt; difficulty thinking, concentrating, or making decisions; or recurrent thoughts of death or suicidal ideation, plans or attempts. To be considered a major depressive episode, a symptom must have clearly worsened compared with the person's preepisode status. The symptoms must persist for most of the day, nearly every day, for at least 2 consecutive weeks. The episode must be accompanied by clinically significant distress or impairment in social, occupational or other important areas of functioning (Diagnostic and Statistical Manual of Mental Disorders 4$^{th}$ Ed. DSM-IV, Pub. American Psychiatric Association, Washington, D.C.; p. 320, 327, 344-345). A "major depressive disorder" generally refers to a single or recurrent Major Depressive Episode which is not better accounted for by Schizophrenia, Delusional Disorder, or Psychotic Disorder Not Otherwise Specified, and also there has never been a Manic Episode, a Mixed Episode or a Hypomanic Episode (Diagnostic and Statistical Manual of Mental Disorders 4$^{th}$ Ed. DSM-IV, Pub. American Psychiatric Association, Washington, D.C.; pp. 344-345). Tables 1, 2 and 3 further define the criteria for Major Depressive Episodes/Disorders: Criteria for Major Depressive Episode (Table 1); a Single Episode of a Major Depressive Disorder (Table 2) and recurrent Major Depressive Disorder (Table 3). The diagnosis is generally based on evaluation by a qualified physician, generally a psychiatrist or by a psychologist. A "minor depressive disorder", also referred to as "dysthymia", has the characteristics of a major depressive disorder but presents itself without the intensity or severity of the symptoms associated with a "major depressive disorder". "Late Life Major Depression", referred to as "LLMD" or "late-onset depression" refers to depression, for example, the major and minor depressive disorders and depressive episodes described above, that occurs in a subject at about 60 years of age or older. The "risk factors" for depression include female gender, unmarried status, having stressful life events and lack of a social support network. Major depressive disorder is characterized by any of a number of symptoms, including persistent sadness or anxiety, or feelings of emptiness, hopelessness, pessimism, guilt, worthlessness, or helplessness.

"Amyloid" describes various types of protein aggregations that share specific traits when examined microscopically. Amyloid is typically identified by a change in the fluorescence intensity of planar aromatic dyes such as Thioflavin T or Congo Red. This is generally attributed to the environmental change as these dyes intercolate between beta-strands. The amyloid fold is characterized by a cross-beta sheet quaternary structure, that is, a monomeric unit contributes a beta strand to a beta sheet which spans across more than one molecule. While amyloid is usually identified using fluorescent dyes, stain polarimetry, circular dichroism, or FTIR (all indirect measurements), the "gold-standard" test to see if a structure is amyloid is by placing a sample in an X-ray diffraction beam; there are two characteristic scattering bands produced at 4 and 10 angstroms each, corresponding to the interstrand distances in the beta sheet structure. The amyloid protein disclosed in the present application refers to amyloid beta, as described below.

"Amyloid beta", "Abeta", "beta-amyloid" or "amyloid beta peptide" is a physiological product normally released from the amyloid beta protein precursor ($\beta$APP or APP) through $\beta$ and $\gamma$ secretase cleavage and consists of two 40 and 42 amino acid peptides, usually abbreviated as A$\beta_{40}$ and A$\beta_{42}$, respectively (Selkoe, D. (2002), J. Clin. Invest. 110: 1375-1381. The 42 amino acid amyloid beta peptide (A$\beta_{42}$) is more hydrophobic & "sticky" (and hence aggregates more readily) than the 40 amino acid amyloid beta peptide (A$\beta_{40}$), and as such may play a greater role in the pathogenesis of Alzheimer's disease, due to its increased tendency to form insoluble fibrils and increased neurotoxicity. Thus, under certain circumstances, as in Alzheimer's disease (AD), brain levels of these peptides increase dramatically, which can lead to the oligomerization of the peptides and eventually to the formation of insoluble fibrillar aggregates, which deposit in senile plaques. In the present application, "amyloid beta$_{40}$" is used interchangeably with "Abeta$_{40}$", AP$_{40}$ and Abeta$_{1-40}$, and "amyloid beta$_{42}$" is used interchangeably with "Abeta$_{42}$", A$\beta_{42}$ and Abeta$_{1-42}$. The nucleic acid and amino acid sequences for amyloid beta precursor protein and A$\beta_{40}$ and A$\beta_{42}$ are found in SEQ ID NOS: 1, 2, 3, 4 and 5. SEQ ID NO: 1 is the nucleic acid sequence encoding human amyloid beta precursor protein; SEQ ID NO: 2 is the nucleic acid encoding human A$\beta_{40}$ peptide; SEQ ID NO: 3 is the amino acid sequence of human A$\beta_{40}$ peptide; SEQ ID NO: 4 is the nucleic acid encoding human A$\beta_{42}$, SEQ ID NO: 5 is the amino acid sequence of human A$\beta_{42}$ peptide.

"Fragment" refers to either a protein or polypeptide comprising an amino acid sequence of at least 4 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues) of the amino acid sequence of a parent protein or polypeptide, or a nucleic acid comprising a nucleotide sequence of at least 10 base pairs (preferably at least 20 base pairs, at least 30 base pairs, at least 40 base pairs, at least 50 base pairs, at least 50 base pairs, at least 100 base pairs, at least 200 base pairs) of the nucleotide sequence of the parent nucleic acid. Any given fragment may or may not possess a functional activity of the parent nucleic acid or protein or polypeptide.

"Combination therapy" refers to the use of the agents of the present invention with other active agents or treatment modalities, in the manner of the present invention for treatment of major depressive disorders. These other agents or treatments may include drugs such as other antidepressants including those that are standardly used to treat various depressive disorders. The agents of the invention may also be combined with corticosteroids, non-steroidal anti-inflammatory compounds, or other agents useful in treating or alleviating pain. The combined use of the agents of the present invention with these other therapies or treatment modalities may be concurrent, or the two treatments may be divided up such that the agent of the present invention may be given prior to or after the other therapy or treatment modality.

"Slow release formulation" refers to a formulation designed to release a therapeutically effective amount of a drug or other active agent such as a polypeptide or a synthetic compound over an extended period of time, with the result being a reduction in the number of treatments necessary to achieve the desired therapeutic effect. In the matter of the present invention, a slow release formulation would decrease the number of treatments necessary to achieve the desired effect in terms of amelioration of, reduction in, or reversal of at least one symptom of the major depressive disorder.

"Surrogate biomarker" or "biomarker" as used herein, refers to a molecule, the existence and levels of which are causally connected to a complex biological process, and reliably captures the state of said process. Furthermore, a surrogate biomarker, to be of practical importance, must be present in samples that can be obtained from individuals without endangering their physical integrity or well-being, preferentially from biological fluids such as blood, urine, saliva or tears.

An "antidepressant" is a medication used primarily in the treatment of clinical depression. Modern antidepressants are not stimulants and are not generally addictive. They also are not thought to produce tolerance, although sudden withdrawal may produce adverse effects. Antidepressants create little if any immediate change in mood and require between several days and several weeks to take effect. There are several different compounds that act as antidepressants. These have different mechanisms of action as well as different chemical structures, many of which are described herein.

"Selective serotonin reuptake inhibitors" or "SSRIs", as described herein, are a class of antidepressants. They act within the brain to increase the amount of the neurotransmitter serotonin (5-hydroxytryptamine or 5-HT) in the synaptic gap by inhibiting its re-uptake.

"Tricyclic antidepressants", as described herein, are a class of antidepressant drugs named after the drugs' molecular structure, which contains three rings of atoms. The term 'tricyclic antidepressant' is sometimes abbreviated to TCA. Most tricylic antidepressants work by inhibiting the re-uptake of the neurotransmitters norepinephrine and serotonin by nerve cells. They are not considered addictive and have many fewer side-effects and restrictions than the MAOIs.

"Monoamine Oxidase Inhibitors" or "MAOIs", as described herein, are a class of antidepressant drugs that act to inhibit the activity of the enzyme monoamine oxidase, an enzyme that is found in many parts of the body. In the brain, monoamine oxidase destroys neurotransmitters, such as norepinephrine and serotonin. MAO inhibitors, by limiting the activity of monoamine oxidase, block the breakdown of those neurotransmitters. They work more quickly than the tricyclics, but they have more severe side effects and require a change in diet.

A "subject at risk for developing a major or minor depressive disorder" or a "subject at risk for developing a major or minor depressive episode", as described herein, refers to a subject who is predisposed to development of a major depressive disorder as described in the present application, by virtue of a past history of such episodes. The occurrence of such episodes may or may not be related to a particular identifiable stressor, which leads to development of such depressive disorder.

"Monitoring the effect of therapy administered to a subject" as used herein refers to a situation whereby a subject is being treated for a major or minor depressive disorder through use of at least one of the drugs described herein for clinical depression, and it is desirable to determine whether there are any benefits to such treatment. The effects of such therapy may be determined by evaluating the subject using standard procedures for such evaluation by a trained physician, preferably a psychiatrist or clinical psychologist. Well known rating scales for depression are used, such as the Hamilton scale, whereby a score of 15 or greater is necessary to establish the presence of significant depressive symptoms associated with major depression that may warrant pharmacological intervention. A 50% reduction in the Hamilton score is generally considered to be therapeutically responsive. A patient having a score of 7 or less is considered to be in remission.

"Abnormal levels of amyloid beta", especially $Abeta_{1-42}$ as defined herein are established by determining the amount of amyloid beta in the brains or body fluid, such as, urine, CSF, blood (whole blood, blood cells or plasma or serum) of normal patients who do not suffer from a major depressive disorder, and comparing these levels with that of patients who suffer from a major depressive disorder. For example, as shown herein, normal elderly control patients show a level of plasma amyloid beta, in particular, $A\beta_{42}$, of 8.1 pg/ml, whereas depressed elderly patients show a value of plasma amyloid beta, in particular, $A\beta_{42}$, 14.3 pg/ml. The difference between the normal (non-depressed) and depressed population of patients should be significantly different at the 95% confidence limit. However, it is recognized by the present invention that any reduction in plasma amyloid beta is good, particularly, $Abeta_{1-42}$, and thus, even a modest lowering (although perhaps not statistically significant when compared to normals) will have an impact on a major depressive disorder or episode.

General Description

Major depressive episode has been reported to be associated with higher rates of neuroradiological abnormalities including deep white matter lesions, cognitive impairment, and an increased risk for Alzheimer's disease (AD). However, the biological mechanisms underlying the development of symptoms and for the higher rates of structural brain abnormalities and for the increased risk for Alzheimer's disease (AD) are not known. The present invention relates to the finding of elevated plasma amyloid beta peptide ($A\beta_{42}$) levels in non-demented, non-Alzheimer's disease (AD) patients suffering from late life major depression (LLMD), which were also associated with greater white matter abnormalities. While the $A\beta_{42}$ peptide has been shown to play a major role in the pathogenesis in AD and elevated plasma $A\beta_{42}$ levels have been associated with increased risk for AD and white matter abnormalities, there have been no previous reports of elevated plasma $A\beta_{42}$ levels in non-demented, non-AD elderly patients suffering from late life major depression. The finding of elevated plasma $A\beta_{42}$ in LLMD could serve as a potential biological marker for the development of depressive symptoms and for an increased risk for brain abnormalities and development of a major depressive episode/disorder. Furthermore, since $A\beta_{42}$ has been shown to be neurotoxic, the finding of elevated levels of $A\beta_{42}$ in the peripheral circulation of patients suffering from depressive episodes/disorders may explain why these patients are more prone to development of Alzheimer's disease. Although patients suffering from Alzheimer's disease exhibit high levels of aggregated, insoluble $A\beta$ fibrils deposited in the brain, which are believed to be neurotoxic and possibly causative of the dementia and cognitive impairment in these patients, the inventors of the present application propose that circulating levels of Abeta, especially $A\beta_{42}$, and in all likelihood other soluble amyloid beta fragments that are capable of crossing the blood brain barrier (BBB), also result in neurotoxicity and disruption of serotoninergic, noradrenergic and dopaminergic neurons (Gonzalo-Ruiz, A. et al., (2003), J. Chemical Neuroanatomy 26: 153-169), which have been implicated in depression even though such fragments and soluble forms of amyloid beta need not necessarily be deposited in the brain. Thus, it is believed that circulating oligomeric forms of $A\beta_{42}$ can cross the blood brain barrier and be neurotoxic and may result in, or be conducive to, the initiation of a major depressive disorder/episode. Furthermore, the findings presented herein may explain why patients suffering from a major depressive episode/disorder are prone to future development of Alzheimer's disease, cognitive dysfunction and dementia.

A number of studies have found an association between cognitive impairment, AD or dementia, and depressed mood or late-life major depression (LLMD). In a meta-analysis of case-control and prospective longitudinal studies of depression and dementia (Jorm, A F. (2001), History of depression as a risk factor for dementia: an updated review. *Australian and New Zealand Journal of Psychiatry.* 35:776-781), it was concluded that depressed individuals are, on average, nearly twice as likely to develop dementia, often in the form of AD, relative to non-depressed controls. For example, one prospective longitudinal study (Devanand, D. P., Sano, M., Tang, M. X., Taylor, S., Gurland, B. J., Wilder, D., Stern, Y., and Mayeux, R. (1996), Depressed mood and the incidence of Alzheimer's disease in the elderly living in the community. *Arch Gen Psychiatry* 53:175-182) found that the presence of depressed mood at baseline was significantly associated with a moderately increased likelihood of incident dementia. Since 93% of the individuals who developed dementia during the follow-up also met the National Institute of Neurological and Communicative Disorders and Stroke—Alzheimer's Disease and Related Disorders Association criteria (NINCDS/ADRDA) for possible or probable AD, the increased likelihood applied predominantly to AD. Excluding individuals who had a form of dementia other than Alzheimer's Disease did not alter the results. Furthermore, limiting the analyses to include only individuals who were cognitively intact at baseline did not attenuate the relationship between LLMD and incident AD. Another well-designed study (Wilson R. S., Barnes L. L., Mendes de Leon C. F., Aggarwal N. T., Schneider J. S., Bach J., Pilat J., Beckett L. A., Arnold S. E., Evans D. A., and Bennett D. A. (2002), Depressive symptoms, cognitive decline, and risk of AD in older persons. *Neurology* 59:364-370) examined the association of depressive symptoms and likelihood for the development of clinical AD or cognitive decline annually over a 7-year period in 821 (n=554 women) older adults who were not demented at baseline. Proportional hazards models were used to determine whether CES-D scores were related to the likelihood of developing clinical AD. Results revealed that for each 1 point increase in the depressive symptoms, as measured by a 10-item form of the CES-D scale, the relative risk (Odds Ratio) of AD increased by an average of 19%, and annual decline on a global cognitive measure increased by an average of 24%. Similarly, Yaffe et al. (Yaffe, K., Blackwell, T., Gore, R., Sands, L., Reus, V., and Browner, W. S. (1999), Depressive symptoms and cognitive decline in nondemented elderly women: A prospective study. *Arch Gen Psychiatry* 56:425-430) found an inverse relationship between number of depressive symptoms and cognitive change in women who were 65 and older and cognitively intact at baseline. Specifically, in analyses accounting for education, age, health status, baseline cognitive scores, and a variety of health behaviors (i.e. tobacco use and alcohol consumption), women with more depressive symptoms showed significantly greater decline over four-years on the Trails B (attention, sequencing, visual scanning, and mental flexibility), Digit Symbol (attention, psychomotor speed, and perceptual organization), and a modified version of the MMSE test (global cognitive functioning) relative to women with few or no depressive symptoms. Likewise, in another prospective longitudinal analysis of depressed and non-depressed adults aged 59 to 71 who were cognitively intact at baseline (Paterniti, S., Verdier-Taillefer, M. H., Dufouil, C., and Alperovitch, A. (2002), Depressive symptoms and cognitive decline in elderly people: Longitudinal study. *British J Psychiatry* 181:406-410), participants at high risk for clinical depression, as measured by high scores on the CES-D, exhibited significantly greater decline on the MMSE over four-years relative to participants who did not have high scores on the CES-D.

Further support for the relatively strong association between LLMD or depressive symptoms and AD is provided by two recent post-mortem studies. For example, in a longitudinal study that included 80 initially non-demented elderly followed through autopsy (mean age at baseline=80.7, sd=9.3 years; baseline CDR=0), greater depressive symptoms were associated with increased likelihood of a dementia diagnosis (Galvin, J. E., Powlishta, K. K., Wilkins, K., McKeel, D. W., Xiong C., Grant, E., Storandt, M., and Morris, J. C. (2005), Predictors of preclinical Alzheimer's Disease and dementia. *Arch Neurol* 62:758-765). AD was histologically confirmed in 79% of the individuals who developed dementia. Interestingly, the number of cerebral infarcts did not differ between those with dementia and those who remained nondemented through follow-up. Sweet et al.'s post-mortem findings (Sweet, R. A., Hamilton, R. L., Butters, M. A., Mulsant, B. H., Pollock, B. G., Lewis, D. A., Lopez, L. O., DeKosky, S. T., and Reynolds, C. F. $3^{rd}$ (2004), Neuropathologic correlates of late-onset major depression. *Neuropsychopharm* 29: 2242-2250), like those of Galvin et al.'s results (Galvin, J. E., Powlishta, K. K., Wilkins, K., McKeel, D. W., Xiong C., Grant, E., Storandt, M., and Morris, J. C. (2005), Predictors of preclinical Alzheimer's Disease and dementia. *Arch Neurol* 62:758-765), also indicated that AD accounts for most cases of dementia. In this study, all of the subjects had their first depressive episode after the age of 60, met the criteria for LLMD based on the Structured Clinical Interview for DSM-IV (SCID), and were all cognitively intact at baseline (Sweet, R. A., Hamilton, R. L., Butters, M. A., Mulsant, B. H., Pollock, B. G., Lewis, D. A., Lopez, L. O., DeKosky, S. T., and Reynolds, C. F. $3^{rd}$ (2004), Neuropathologic correlates of late-onset major depression. *Neuropsychopharm* 29: 2242-2250). Comprehensive neuropsychological assessments were done annually, and autopsies were performed on 10 subjects. The time interval from the onset of depression to death was 57 months (median). Seven out of 10 individuals developed dementia during the longitudinal follow-up and 6 (86%) out of 7 of these individuals had a pathological diagnosis of AD. It is also noteworthy that 3 out of the four individuals who had significant vascular pathology and all 3 individuals with Lewy bodies also met pathologic criteria for AD. Additionally, only the AD pathology was significantly associated with dementia (p=0.03). To summarize, both of these post-mortem studies confirm the predominance of AD pathology in elderly individuals with depressed moods or late onset LLMD who develop dementia. Overall, the results derived from the aforementioned case studies, prospective longitudinal studies, and post-mortem studies indicated that a substantial number of these individuals developed dementia or exhibited significant cognitive decline within a few years.

The relationship between depression and cognitive decline or AD is not fully understood. Some have argued that depression is associated with reversible cognitive decline. Other studies suggest that LLMD-associated cognitive deficits, particularly executive function, may not necessarily resolve with successful antidepressant treatment and may be associated with subsequent conversion to AD (Alexopoulos, G. S. (2003), Role of executive function in late-life depression. *J Clin Psychiatry* 64 Suppl 14:18-23; Kalayam, B., and Alexopoulos, G. S. (1999), Prefrontal dysfunction and treatment response in geriatric depression. *Arch Gen Psychiatry* 56:713-718). Additionally, there are also emerging data from a variety of neuroimaging techniques consistent with the presence of structural and functional brain abnormalities in individuals with LLMD (Krishnan, K. R., Taylor, W. D., McQuoid, D. R., MacFall, J. R., Payne, M. E., Provenzale, J. M., and Steffens, D. C. (2004), Clinical characteristics of magnetic resonance imaging-defined subcortical ischemic depression. *Biol Psychiatry* 55:390-397; Kumar, A., Gupta, R. C., Albert, T. M, Alger, J., Wyckoff, N., and Hwang, S. (2004), Biophysical changes in normal-appearing white matter and subcortical nuclei in late-life major depression detected using magnetization transfer. *Psychiatry Res* 130: 131-140).

The findings from the aforementioned studies indicated that not every individual with LLMD would go on to develop AD during longitudinal follow-up. For example, in Sweet and colleagues (Sweet, R. A., Hamilton, R. L., Butters, M. A., Mulsant, B. H., Pollock, B. G., Lewis, D. A., Lopez, L. O., DeKosky, S. T., and Reynolds, C. F. 3$^{rd}$ (2004), Neuropathologic correlates of late-onset major depression. *Neuropsychopharm* 29: 2242-2250) post-mortem study, 3 out of the 10 subjects did not develop AD. Accordingly, it would be useful to find a biological marker that would help to identify those individuals with late-onset LLMD who may have prodromal AD. Results from the studies presented herein suggest that elevated plasma A$\beta_{42}$ and greater reductions over time may be useful biomarkers for identifying with late-onset LLMD who may have prodromal AD. The A$\beta$ peptides, especially the 42 amino acid form (A$\beta_{42}$), produced through proteolytic cleavage of the amyloid precursor protein (APP) have been demonstrated to have powerful neurotoxic effects. Elevated brain levels have been implicated in the pathogenesis of AD (Cleary, J. P., Walsh, D. M., Hofmeister, J. J., Shankar, G. M., Kuskowski, M. A., Selkoe, D. J., and Ashe, K. H. (2005), Natural oligomers of the amyloid-beta protein specifically disrupt cognitive function. *Nat Neurosci* 8:79-84; Jhoo, J. H., Kim, H. C., Nabeshima, T., Yamada, K., Shin, E. J., Jhoo, W. K., Kim, W., Kang, K. S., Jo, S. A., and Woo, J. I. (2004), Beta-amyloid (1-42)-induced learning and memory deficits in mice: involvement of oxidative burdens in the hippocampus and cerebral cortex. *Behav Brain Res* 155:185-196; Walsh, D. M., and Selkoe, D. J. (2004), Oligomers on the brain: The emerging role of soluble protein aggregates in neurodegeneration. *Protein Pept Lett* 11:1-16). Results from longitudinal studies involving relatively large numbers of cognitively intact elderly (Mayeux, R., Tang, M. X., Jacobs, D. M., Manly, J., Bell, K., Merchant, C., Small, S. A., Stern, Y., Wisniewski, H. M., and Mehta, P. D. (1999), Plasma amyloid beta-peptide 1-42 and incipient Alzheimer's disease. *Ann Neurol* 46:412-416; Mayeux, R., Honig, L. S., Tang, M. X., Manly, J., Stern, Y., Schupf, N., and Mehta, P. D. (2003), Plasma Abeta$_{40}$ and Abeta$_{42}$ and Alzheimer's disease: relation to age, mortality, and risk. *Neurology* 61:1185-1190), also indicated that elevated plasma A$\beta_{42}$ levels may be a significant risk factor for the development of AD in the general population. Furthermore, prior longitudinal research has also revealed a significant association between A$\beta_{42}$ and cognitive decline (Pomara, N., Willoughby, L., Sidtis, J. J., and Mehta, P. D. (2005), Selective reductions in A$\beta$ 1-42 in healthy elderly subjects during longitudinal follow-up: A preliminary report. *Am J Geriatr Psychiatry* 13:914-917). Specifically, higher baseline A$\beta_{42}$ levels and greater reductions in A$\beta_{42}$ were significantly associated with a greater decline in MMSE scores over four years.

There is also evidence that platelet activation, which is believed to be a major source of plasma A$\beta$ (Chen, M., Inestrosa, N. C., Ross, G. S., and Fernandez, H. L. (1995), Platelets are the primary source of amyloid beta-peptide in human blood. *Biochem Biophys Res Commun* 213: 96-103; Li, Q. X., Berndt, M. C., Bush, A. I., Rumble, B., Mackenzie, I., Friedhuber, A., Beyreuther, K., and Masters, C. L. (1994), Membrane-associated forms of the beta A4 amyloid protein precursor of Alzheimer's disease in human platelet and brain: Surface expression on the activated human platelet. *Blood* 84:133-142) and other APP products, might be increased in individuals with depression (Lagrhrissi-Thode, F., Wagner, W. R., Pollock, B. G., Johnson, P. C., and Finkel M S (1997), Elevated platelet factor 4 and b-thromboglobulin plasma levels in depressed patients with ischemic heart disease. *Biol Psychiatry* 42:290-295; Markovitz, J. H., Shuster, J. L., Chitwood, W. S., May, R. S., and Tolbert, L. C. (2000), Platelet activation in depression and effects of sertraline treatment: An open-label study. *Am J Psychiatry* 157:1006-1008; Musselman, D. L., Tomer, A., Manatunga, A. K., Knight, B. T., Porter, M. R., Kasey, S., Marzec, U., Harker, L. A., and Nemeroff, C. B. (1996), Exaggerated platelet reactivity in major depression. *Am J Psychiatry* 153:1313-1317; Piletz, J. E., Zhu, H., and Madakasira, S. (2000), Elevated p-selectin on platelets in depression: Response to bupropion. *J Psychiatric Res* 34:397-404; Pollock, B. G., Laghrissi-Thode, F., and Wagner, W. R. (2000), Evaluation of platelet activation in depressed patients with ischemic heart disease after paroxetine or nortriptyline treatment. *J Clin Psychopharmacol* 20:137-140). While the findings noted above raised the possibility that elevated plasma A$\beta$ levels could occur in individuals with LLMD and contribute to the increased susceptibility to AD and brain abnormalities associated with this disorder, the data presented herein demonstrate that there is no relationship between platelet activation and A$\beta$ levels in patients having LLMD. Similar findings were also reported by Olsson, A. et al. (Olsson, A. et al. (2003), Unaltered plasma levels of beta-amyloid (1-40) and Beta amyloid (1-42) upon stimulation of human platelets. *Dement Geriatr Cogn Disord* 16(2):93-7).

The results from a clinical study are shown herein, whereby the inventor examined whether plasma A$\beta$ levels in elderly individuals with LLMD differed from nondepressed controls and whether they were associated with age of onset of first depressive episode, antidepressant treatment, and indices of platelet activation and brain abnormalities. Since elevated A$\beta_{42}$ is associated with cognitive decline and incident AD, the finding of elevated $A\beta_{42}$ in elderly depressives might provide a useful approach for further investigation of the utility of $A\beta_{42}$ to identify individuals with LLMD who might develop subsequent cognitive decline and AD. Furthermore, the presence of elevated circulating levels of Aβ42 may prove to be a non-invasive means of assessing an individual's risk of developing late onset depression and depressive symptoms, or may be identified as a causative biological factor for the development of depressive symptoms and disorders.

Accordingly, the present invention relates in general to the identification of elevated levels of amyloid beta in tissues and/or body fluids of patients suffering from a major depressive disorder. More particularly, the invention relates to the identification of elevated levels of amyloid beta in blood, more particularly plasma, from non-demented, non-AD, elderly depressed patients.

In addition, the present invention provides for amyloid beta as a biomarker of clinical depression. In accordance with the present invention, the amyloid beta protein or fragments thereof, can be obtained using minimally invasive procedures. In a particular aspect, the invention provides for methods of screening, diagnosis or prognosis of a major depressive disorder in a subject, or for identifying a subject at risk for developing a major depressive disorder, or for monitoring the effect of therapy administered to a subject having a major depressive disorder. In a particular embodiment, the method comprises the steps of:

a. collecting a biological test sample from said subject;
b. analyzing said test sample for the presence of amyloid beta levels; and
c. comparing the level of amyloid beta in the test sample with the level of amyloid beta in one or more persons free from a major depressive disorder, or with a previously determined reference range for amyloid beta established from subjects free of major depressive disorder.

While the amyloid beta or fragment thereof may be measured in any bodily tissue sample from the subject, it is desirable to perform the measurement from a sample of bodily fluid, such as, but not limited to whole blood, blood cells, serum, plasma, urine and cerebrospinal fluid (CSF). In this manner, the sample may be obtained by non-invasive or minimally invasive procedures. Thus, the determination of elevated levels of amyloid beta in the sample from a patient who potentially has a major depressive disorder or who is prone to development of a major depressive disorder can be made and such measurement can be used as a surrogate marker for determination of a major depressive disorder. Accordingly, in one particular embodiment, an elevation of amyloid beta in a subject correlates with the presence of a major depressive disorder. In another particular embodiment, the amyloid beta is $Abeta_{40}$ or $Abeta_{42}$ and the elevation of amyloid beta is the result of an increase in production or generation of $Abeta_{40}$ or $Abeta_{42}$ as determined by measurement of $Abeta_{40}$ or $Abeta_{42}$ in a 24 hour urine sample. The level of amyloid beta may be measured by standard immunological and/or biochemical assays known to one skilled in the art, such as enzyme-linked immunosorbent assays (ELISA), Western blot assays, Northern blot assays, and Southern blot assays.

In another particular embodiment, the quantitative method comprises testing at least one aliquot of the test sample, comprising the steps of:

a. contacting the aliquot with an antibody that is immuno-specific for amyloid beta;
b. quantitatively measuring any binding that has occurred between the antibody and the test sample.

The methods of the present invention provide for use of an antibody that binds to (is specific for) amyloid beta, $Abeta_{40}$, $Abeta_{42}$ or fragments thereof and may be a monoclonal or polyclonal antibody specific for amyloid beta, in particular, amyloid $beta_{1-40}$ or amyloid $beta_{1-42}$. In a particular embodiment, the step of quantitatively measuring comprises testing a plurality of aliquots with a plurality of antibodies for the quantitative detection of amyloid beta.

Another aspect of the invention provides a method of identifying a subject at risk for developing a major depressive disorder, said method comprising:

a) collecting a test sample from said subject;
b) analyzing said test sample for the presence of amyloid beta levels; and
c) comparing the level of amyloid beta in the test sample with the level of amyloid beta in one or more persons free from a major depressive disorder, or with a previously determined reference range for amyloid beta established from subjects free of a major depressive disorder.

In a particular embodiment, the amyloid beta is amyloid $beta_{1-40}$ or amyloid $beta_{1-42}$ or fragments thereof. In another particular embodiment, the test sample is selected from the group consisting of whole blood, blood cells, serum, plasma, urine and cerebrospinal fluid (CSF).

Another aspect of the invention provides a diagnostic test for assessing a subject's risk of developing or having a major or minor depressive disorder in a subject in which abnormal levels of amyloid beta are associated with the major or minor depressive disorder, or for establishing a response to therapy for said condition, said diagnostic test comprising the following steps:

a) collecting one tissue or cellular sample from said subject;
b) measuring the level of amyloid beta in said one tissue or cellular sample and comparing the levels of amyloid beta with a range of predetermined values for amyloid beta, said values having been determined as falling within a reference range of amyloid beta, and wherein said level of amyloid beta is evaluated in conjunction with other risk factors for said major or minor depressive disorder, said evaluation then being used to determine the subject's risk profile for said major or minor depressive disorder;

wherein said comparing provides information for assessing a subject's risk of developing or having a major or minor depressive disorder in which abnormal levels of amyloid beta are associated with said major or minor depressive disorder, or for establishing a prognosis for response to therapy for said condition, if the values of amyloid beta obtained from said one tissue or cellular sample fall outside of the normal range of amyloid beta, and if the level of amyloid beta correlates with the presence of one or more risk factors for said major or minor depressive disorder.

In a particular embodiment, the amyloid beta is amyloid $beta_{1-40}$ or amyloid $beta_{1-42}$ or fragments thereof. In another particular embodiment, the test sample is selected from the group consisting of whole blood, blood cells, serum, plasma, urine and CSF.

Another aspect of the invention provides a method of measuring the effectiveness of a pharmaceutical composition comprising an agent for treating a subject having a major or minor depressive disorder, comprising the steps of:

a) determining the level of amyloid beta in a biological test sample obtained from the subject;

b) administering an amount of a pharmaceutical composition comprising said agent to the patient;
c) repeating step a) using a subsequently-collected biological sample obtained from the subject;
d) comparing the level of amyloid beta determined in step a) with the level of amyloid beta determined in step c), wherein the effectiveness of the pharmaceutical composition is monitored by detecting a decrease in the level of amyloid beta in the subsequently-collected biological sample compared with the biological sample from step a).

In a particular embodiment, the amyloid beta is amyloid beta$_{1-40}$ or amyloid beta$_{1-42}$ or fragments thereof. In another particular embodiment, the test sample is selected from the group consisting of whole blood, blood cells, serum, urine, CSF and plasma.

Screening Methods for Measuring Amyloid Beta Levels

Antibodies to Amyloid Beta for Therapeutic or Diagnostic Use

According to the present invention, amyloid beta, including abeta$_{40}$ and abeta$_{42}$, as produced by a recombinant source, or through chemical synthesis, or isolated from natural sources; and derivatives, analogs and fragments thereof, including fusion proteins, may be used as an immunogen to generate antibodies that recognize amyloid beta, as exemplified below. Such antibodies include but are not limited to polyclonal, monoclonal, chimeric including humanized chimeric, single chain, Fab fragments, and a Fab expression library. The anti-amyloid beta antibodies, for example, of the invention may be cross reactive, that is, they may recognize an amyloid beta derived from a different source. Polyclonal antibodies have greater likelihood of cross reactivity. Alternatively, an antibody of the invention may be specific for a single form of amyloid beta, such as the human amyloid beta proteins amyloid beta$_{40}$ or amyloid beta beta$_{42}$, or a fragment of a human amyloid beta protein.

Various procedures known in the art may be used for the production of polyclonal antibodies to amyloid beta or derivatives, analogs or fragments thereof. For the production of an antibody, various host animals can be immunized by injection with amyloid beta, or a derivative (e.g., or fusion protein) thereof, including but not limited to rabbits, mice, rats, sheep, goats, etc. In one embodiment, amyloid beta or a fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies directed toward amyloid beta, or analogs, derivatives or fragments thereof, any technique that provides for the production of antibody molecules by continuous cell lines in culture may be used. These include but are not limited to the hybridoma technique originally developed by Kohler and Milstein (*Nature*, 256: 495-497 (1975)), as well as the trioma technique, the human B-cell hybridoma technique (Kozbor et al., *Immunology Today*, 4:72 (1983); Cote et al., *Proc. Natl. Acad. Sci. U.S.A.*, 80:2026-2030 (1983)), and the EBV-hybridoma technique to produce human monoclonal antibodies (Cole et al., in *Monoclonal Antibodies and Cancer Therapy*, Alan R. Liss, Inc., pp. 77-96 (1985)). In an additional embodiment of the invention, monoclonal antibodies can be produced in germ-free animals utilizing recent technology (PCT/US90/02545). In fact, according to the invention, techniques developed for the production of "chimeric antibodies" (Morrison et al., *J. Bacteriol.*, 159:870 (1984); Neuberger et al., *Nature*, 312:604-608 (1984); Takeda et al., *Nature*, 314:452-454 (1985)) by splicing the genes from a mouse antibody molecule specific for amyloid beta together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. Nos. 5,476,786 and 5,132,405 to Huston; U.S. Pat. No. 4,946,778) can be adapted to produce e.g., amyloid beta-specific single chain antibodies. An additional embodiment of the invention utilizes the techniques described for the construction of Fab expression libraries (Huse et al., *Science*, 246:1275-1281 (1989)) to allow rapid and easy identification of monoclonal Fab fragments with the desired specificity for amyloid beta, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. Once the antibody is produced, the antibody may be employed in the assays noted above to screen bodily tissues or fluids for the presence of amyloid beta or fragments thereof. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of amyloid beta, one may assay generated hybridomas for a product which binds to the amyloid beta or fragment containing such epitope and choose those which do not cross-react with amyloid beta. For selection of an antibody specific to amyloid beta from a particular source, one can select on the basis of positive binding with amyloid beta expressed by or isolated from that specific source.

The foregoing antibodies can be used in methods known in the art relating to the localization and activity of the amyloid beta, e.g., for Western blotting, imaging amyloid beta in situ, measuring levels thereof in appropriate physiological samples, etc. using any of the detection techniques mentioned herein or known in the art. The standard techniques known in the art for immunoassays are described in "Methods in Immunodiagnosis", 2nd Edition, Rose and Bigazzi, eds. John Wiley & Sons, 1980; Campbell et al., "Methods and Immunology", W.A. Benjamin, Inc., 1964; and Oellerich, M. (1984) J. Clin. Chem. Clin. Biochem. 22:895-904.

In a specific embodiment, antibodies that agonize or antagonize the activity of amyloid beta can be generated. Such antibodies can be tested using the assays described infra for identifying ligands.

One aspect of the invention provides a method of using an antibody against amyloid beta, for example $Abeta_{1-42}$, to diagnose a major depressive disorder in a subject. As amyloid beta levels correlate with the presence of a major depressive episode/disorder in a subject, with the presence of a major episode/depressive disorder being determined by a psychiatric evaluation based on the presence of DSM-IV criteria for Major Depressive Episodes and the presence of significant depressive symptoms as determined by a psychiatric rating scale such as the Hamilton scale, amyloid beta serves as a general biomarker for a major depressive disorder, and may be predictive of the future onset of such disorder. Alternatively, it may also serve as a marker for monitoring efficacy of therapy for such disorder, as described herein. Thus, the antibody compositions and methods provided herein are particularly deemed useful for the diagnosis of a major depressive disorder. In a particular embodiment, the major depressive disorder is the result of build-up of amyloid beta in the brains of individuals suffering from such major depressive disorder. More particularly, the amyloid beta is $abeta_{40}$ and $abeta_{42}$.

The diagnostic method of the invention provides contacting a biological sample such as a biopsy sample, tissue, cell or fluid (e.g., whole blood, plasma, serum, urine, or CSF) isolated from a subject with an antibody which binds amyloid beta (Ghiso et al. FEBS Letters 408 (1997) pages 105-108). The antibody is allowed to bind to the antigen to form an antibody-antigen complex. The conditions and time required to form the antibody-antigen complex may vary and are dependent on the biological sample being tested and the method of detection being used. Once non-specific interactions are removed by, for example, washing the sample, the antibody-antigen complex is detected using any one of the immunoassays described above as well a number of well-known immunoassays used to detect and/or quantitate antigens (see, for example, Harlow and Lane, Antibodies: A Laboratory Manual, Cold Spring Harbor Laboratory, New York (1988) 555-612). Such well-known immunoassays include antibody capture assays, antigen capture assays, and two-antibody sandwich assays. In an antibody capture assay, the antigen is attached to solid support, and labeled antibody is allowed to bind. After washing, the assay is quantitated by measuring the amount of antibody retained on the solid support. In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that binds to the antigen.

These immunoassays typically rely on labeled antigens, antibodies, or secondary reagents for detection. These proteins may be labeled with radioactive compounds, enzymes, biotin, or fluorochromes. Of these, radioactive labeling may be used for almost all types of assays. Enzyme-conjugated labels are particularly useful when radioactivity must be avoided or when quick results are needed. Biotin-coupled reagents usually are detected with labeled streptavidin. Streptavidin binds tightly and quickly to biotin and may be labeled with radioisotopes or enzymes. Fluorochromes, although requiring expensive equipment for their use, provide a very sensitive method of detection. Those of ordinary skill in the art will know of other suitable labels which may be employed in accordance with the present invention. The binding of these labels to antibodies or fragments thereof may be accomplished using standard techniques such as those described by Kennedy, et al. ((1976) Clin. Chim. Acta 70:1-31), and Schurs, et al. ((1977) Clin. Chim Acta 81:1-40).

In accordance with the diagnostic method of the invention, the presence or absence of the antibody-antigen complex is correlated with the presence or absence in the biological sample of the antigen, or a peptide fragment thereof. A biological sample containing elevated levels of said antigen (amyloid beta) is indicative of a major depressive disorder in a subject from which the biological sample was obtained. Accordingly, the diagnostic method of the invention may be used as part of a routine screen in subjects suspected of having a major depressive disorder or for subjects who may be predisposed to having a major depressive disorder. Moreover, the diagnostic method of the invention may be used alone or in combination with other well-known diagnostic methods to confirm the presence of a major depressive disorder.

The diagnostic method of the invention further provides that an antibody of the invention may be used to monitor the levels of amyloid beta antigen in patient samples at various intervals of drug treatment to identify whether and to which degree the drug treatment is effective in reducing or inhibiting the symptoms associated with such depressive disorder, such reduction being an indication that the therapy may ultimately result in amelioration and/or cure of the disorder. Furthermore, antigen levels may be monitored using an antibody of the invention in studies evaluating efficacy of drug candidates in model systems and in clinical trials. The antigens provide for surrogate biomarkers in biological fluids to non-invasively assess the global status of the major depressive disorder. For example, using an antibody of this invention, antigen levels may be monitored in biological samples of individuals treated with known or unknown therapeutic agents or toxins. This may be accomplished with cell lines in vitro or in model systems and clinical trials, depending on the depressive disorder being investigated. Persistently increased total levels of amyloid beta antigen in biological samples during or immediately after treatment with a drug candidate indicates that the drug candidate has little or no effect on cell proliferation. Likewise, the reduction in total levels of amyloid beta antigen indicates that the drug candidate is effective in reducing or inhibiting the symptoms of the major depressive disorder. Furthermore, the continued reduction of amyloid beta in the subject may ultimately result in full remission of the individual suffering from such depressive disorder. This may provide valuable information at all stages of pre-clinical drug development, clinical drug trials as well as subsequent monitoring of patients undergoing drug treatment.

Antibody Labels

The amyloid beta proteins of the present invention, antibodies to amyloid beta proteins, and nucleic acids that hybridize to amyloid beta genes (e.g. probes) etc. can all be labeled. Suitable labels include enzymes, fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. Such labels may also be appropriate for the nucleic acid probes used in binding studies with amyloid beta. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. ultraviolet light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70:419-439 (1980) and in U.S. Pat. No. 4,857,453.

Suitable enzymes include, but are not limited to, alkaline phosphatase and horseradish peroxidase.

In addition, amyloid beta, or a fragment thereof can be modified to contain a marker protein such as green fluorescent protein as described in U.S. Pat. No. 5,625,048 filed Apr. 29, 1997, WO 97/26333, published Jul. 24, 1997 and WO 99/64592 all of which are hereby incorporated by reference in their entireties.

Other labels for use in the invention include magnetic beads or magnetic resonance imaging labels.

In another embodiment, a phosphorylation site can be created on an antibody of the invention for labeling with $^{32}$P, e.g., as described in European Patent No. 0372707 (application No. 89311108.8) by Sidney Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as [$^{35}$S]-methionine or [$^{32}$P]-orthophosphate. In addition to metabolic (or biosynthetic) labeling with [$^{35}$S]-methionine, the invention further contemplates labeling with [$^{14}$C]-amino acids and [$^3$H]-amino acids (with the tritium substituted at non-labile positions).

Quantification of amyloid beta can also be done using staining with Congo red with subsequent image analysis (Kindy, M S et al. (1998), Am. J. Pathol. 152: 1387-1395; Kisilevsky, R. et al. (1995), Nat. Med. 1:143-148).

Other Diagnostic Means for Determining Levels of Amyloid Beta

Cell-Based Reporters and Instrumentation

Cellular screening techniques can be broadly classified into two groups: semi-biochemical approaches that involve the analysis of cell lysates, or live cell assays. Whole cell assay methodologies vary with respect to assay principle, but have largely in common a form of luminescence or fluorescence for detection. Luminescence is a phenomenon in which energy is specifically channeled to a molecule to produce an excited state. Luminescence includes fluorescence, phosphorescence, chemiluminescence and bioluminescence.

An ever-increasing list of fluorescent proteins includes the widely-used GFP derived from Aequorea Victoria and spectral variants thereof. The list includes a variety of fluorescent proteins derived from other marine organisms; bacteria; fungi; algae; dinoflagellates; and certain terrestrial species. These reporters have the advantage of not requiring any exogenous substrates or co-factors for the generation of a signal but do require an external source of radiation for excitation of the intrinsic fluorophore. In addition, the increasing availability of genes encoding a broad spectrum of fluorescent reporter proteins enables the construction of assays tailored for specific applications, cell types, and detection systems.

Different classes of luminescent proteins, luciferases, have been have been discovered in bacteria and eukaryotes. Luciferases are proteins that catalyze the conversion of a natural substrate into a product that emits light in the visible spectrum and thus require no external radiation source. Monomeric forms of luciferase have been cloned from firefly, Renilla, and other organisms. Firefly luciferase is the most common of the bioluminescent reporters and is a 61 kDa monomeric enzyme that catalyzes a two-step oxidation reaction to yield light. Renilla luciferase is a 31 kDa monomeric enzyme that catalyzes the oxidation of coelenterazine to yield coelenteramide and blue light of 480 nm. Substrates for luciferase are widely available from commercial suppliers such as Promega Corporation and Invitrogen Molecular Probes.

A variety of useful enzymatic reporters are enzymes that either generate a fluorescent signal or are capable of binding small molecules that can be tagged with a fluorescent moiety to serve as a fluorescent probe. For example, dihydrofolate reductase (DHFR) is capable of binding methotrexate with high affinity; a methotrexate-fluorophore conjugate can serve as a quantitative fluorescent reagent for the measurement of the amount of DHFR within a cell. By tagging methotrexate with any of a number of fluorescent molecules such as fluorescein, rhodamine, Texas Red, BODIPY and other commercially available molecules (such as those available from Molecular Probes/Invitrogen and other suppliers) a range variety of fluorescent readouts can be generated. The wide range of techniques of immunohistochemistry and immunocytochemistry can be applied to whole cells. For example, ligands and other probes can be tagged directly with fluorescein or another fluorophore for detection of binding to cellular proteins; or can be tagged with enzymes such as alkaline phosphatase or horseradish peroxidase to enable indirect detection and localization of signal.

Many other enzymes can be used to generate a fluorescent signal in live cells by using specific, cell-permeable substrate that either becomes fluorescent or shifts its fluorescence spectrum upon enzymatic cleavage. For example, substrates for beta-lactamase exist whose fluorescence emission properties change in a measurable way upon cleavage of a beta-lactam core moiety to which fluorophores are attached. Changes include, shifts in fluorophore absorption or emission wavelengths, or cleavage of a covalent assembly of emmision-absorption-mathched fluorophore pairs that in the covalently-assembled form sustain resonance energy transfer between the two fluorophores that is lost when the two are separated. Membrane-permeant, fluorescent BLA substrates such as the widely-used CCF2/AM allow the measurement of gene expression in live mammalian cells in the absence or presence of compounds from a biologically active chemical library.

Luminescent, fluorescent or bioluminescent signals are easily detected and quantified with any one of a variety of automated and/or high-throughput instrumentation systems including fluorescence multi-well plate readers, fluorescence activated cell sorters (FACS) and automated cell-based imaging systems that provide spatial resolution of the signal. A variety of instrumentation systems have been developed to automate HCS including the automated fluorescence imaging and automated microscopy systems developed by Cellomics, Amersham, TTP, Q3DM, Evotec, Universal Imaging and Zeiss. Fluorescence recovery after photobleaching (FRAP) and time lapse fluorescence microscopy have also been used to study protein mobility in living cells. Although the optical instrumentation and hardware have advanced to the point that any bioluminescent signal can be detected with high sensitivity and high throughput, the existing assay choices are limited either with respect to their range of application, format, biological relevance, or ease of use.

Transcriptional Reporter Assays

Cell-based reporters are often used to construct transcriptional reporter assays, which allow monitoring of the cellular events associated with signal transduction and gene expression. Reporter gene assays couple the biological activity of a target to the expression of a readily detected enzyme or protein reporter. Based upon the fusion of transcriptional control elements to a variety of reporter genes, these systems "report" the effects of a cascade of signaling events on gene expression inside cells. Synthetic repeats of a particular response element can be inserted upstream of the reporter gene to regulate its expression in response to signaling molecules generated by activation of a specific pathway in a live cell. The variety of transcriptional reporter genes and their application is very broad and includes drug screening systems based on beta-galactosidase (beta-gal), luciferase, alkaline phosphatase (luminescent assay), GFP, aequorin, and a variety of newer bioluminescent or fluorescent reporters.

In general, transcription reporter assays have the capacity to provide information on the response of a pathway to natural or synthetic chemical agents on one or more biochemical pathways, however they only indirectly measure the effect of an agent on a pathway by measuring the consequence of pathway activation or inhibition, and not the site of action of the compound. For this reason, mammalian cell-based methods have been sought to directly quantitate protein-protein interactions that comprise the functional elements of cellular biochemical pathways and to develop assays for drug discovery based on these pathways.

Cellular Assays for Individual Proteins Tagged with Fluorophores or Luminophores.

Subcellular compartmentalization of signaling proteins is an important phenomenon not only in defining how a biochemical pathway is activated but also in influencing the desired physiological consequence of pathway activation. This aspect of drug discovery has seen a major advance as a result of the cloning and availability of a variety of intrinsically fluorescent proteins with distinct molecular properties.

High-content (also known as high-context) screening (HCS) is a live cell assay approach that relies upon image-based analysis of cells to detect the subcellular location and redistribution of proteins in response to stimuli or inhibitors of cellular processes. Fluorescent probes can be used in HCS; for example, receptor internalization can be measured using a fluorescently-labeled ligand that binds to the transferrin receptor. Often, individual proteins are either expressed as fusion proteins, where the protein of interest is fused to a detectable moiety such as GFP, or are detected by immunocytochemistry after fixation, such as by the use of an antibody conjugated to Cy3 or another suitable dye. In this way, the subcellular location of a protein can be imaged and tracked in real time. One of the largest areas of development is in applications of GFP color-shifted mutants and other more recently isolated new fluorescent proteins, which allow the development of increasingly advanced live cell assays such as multicolor assays. A range of GFP assays have been developed to analyze key intracellular signaling pathways by following the redistribution of GFP fusion proteins in live cells. For drug screening by HCS the objective is to identify therapeutic compounds that block disease pathways by inhibiting the movement of key signaling proteins to their site of action within the cell.

Tagging a protein with a fluorophore or a luminophore enables tracking of that particular protein in response to cell stimuli or inhibitors. For example, the activation of cell signaling by TNF can be detected by expressing the p65 subunit of the NFkB transcription complex as a GFP fusion and then following the redistribution of fluorescence from the cytosolic compartment to the nuclear compartment of the cell within minutes after TNF stimulation of live cells (J A Schmid et al., 2000, Dynamics of NFkB and IkBa studied with green fluorescent protein (GFP) fusion proteins, J. Biol. Chem. 275: 17035-17042). What has been unique about these approaches is the ability to allow monitoring of the dynamics of individual protein movements in living cells, thus addressing both the spatial and temporal aspects of signaling.

Methods of Treating a Major Depressive Disorder

Another aspect of the invention provides for methods of treating and/or preventing a major depressive disorder comprising administering a therapeutically effective amount of an agent that reduces brain amyloid beta levels. Such reduction of brain amyloid beta levels may be the result of treatment with an agent which either prevents the production or generation of amyloid beta (such production or generation occurring through the cleavage of beta amyloid precursor protein or APP), or which prevents the aggregation of amyloid beta fibrils and deposition in cerebral parenchymal tissues and blood vessels, or by preventing the formation of the oligomeric forms of Abeta, $Abeta_{1-40}$ or $Abeta_{1-42}$, or which increases the degradation of amyloid beta, or which increases the clearance of amyloid beta from the brain, or which facilitates the peripheral metabolism and clearance of amyloid beta. In another aspect the method of treating or preventing a major depressive disorder comprises administration of an agent that might prevent or interfere with Abeta-induced neurotoxicity. In a particular embodiment, the amyloid beta is amyloid $beta_{1-40}$ or amyloid $beta_{1-42}$ or fragments thereof. In another embodiment of the present invention, it is envisioned that circulating levels of amyloid beta, including $Abeta_{40}$ or $Abeta_{42}$ and oligomeric forms may be damaging (eg. neurotoxic) even if not deposited. That is, the present invention contemplates that soluble, non-fibrillary forms of Abeta, in particular, $Abeta_{1-42}$ may be neurotoxic and can lead to neuronal damage or alterations in neurotransmitter levels or perturbations in neurotransmission through interference with signaling systems, the result of which is a Major Depressive Episode or Disorder. Accordingly, the levels of circulating Abeta as found in plasma or whole blood may be diagnostic of a Major Depressive Disorder or Episode or predictive of a risk for developing such disorders. The studies shown herein have demonstrated that elevated $Abeta_{42}$ can be found in the plasma of both early onset depressive patients (before the age of 60) as well as late onset depressive patients (after the age of 60), thus suggesting that elevated plasma $Abeta_{42}$ levels may play a role in depressive symptoms and depressive episodes/disorders in the young as well as the elderly population. Thus, treatment strategies contemplated for the elderly with respect to the lowering of Abeta, or for interfering with Abeta-mediated neurotoxicity, especially $Abeta_{1-42}$, are also contemplated for the younger population wherein higher than normal levels of Abeta are associated with a Major Depressive Episode/Disorder.

Another aspect of the invention provides for combination therapy with an agent that reduces brain amyloid beta and use of at least one other (a second) therapeutic agent. In a preferred embodiment, a composition comprising an agent/compound that reduces brain amyloid beta is administered concurrently with the administration of a second therapeutic agent, which can be part of the same composition as or in a different composition from that comprising the agent/compound that reduces brain amyloid beta. In another embodiment, a composition comprising a compound that reduces brain amyloid beta is administered prior or subsequent to administration of a second therapeutic agent. As many of the disorders for which the compounds of the invention are useful in treating are chronic, in one embodiment combination therapy involves alternating between administering a composition comprising a compound that reduces brain amyloid beta and a composition comprising a second therapeutic agent, e.g., to minimize the toxicity associated with a particular drug. The duration of administration of the agent/compound that reduces brain amyloid beta or and/or second therapeutic agent can be, e.g., one month, three months, six months, a year, or for more extended periods, or on an alternate or intermittent schedule. In certain embodiments, when a compound that reduces brain amyloid beta is administered concurrently with a second therapeutic agent that potentially produces adverse side effects including, but not limited to, toxicity, the second therapeutic agent can advantageously be administered at a dose that falls below the threshold at which the adverse side is elicited. In another particular embodiment, the second drug that is used is effective at treating a major depressive disorder. In yet another particular embodiment, the second drug is administered concurrently, prior to, or after the agent that reduces brain amyloid beta levels. In yet another particular embodiment, the second drug is selected from the group consisting of Selective Serotonin Reuptake Inhibitors (SSRI), tricyclic antidepressants, and monoamine oxidase (MAO) inhibitors. In a more particular embodiment, the Selective Serotonin Reuptake Inhibitor is selected from the group consisting of citalopram, escitalopram HBr, fluvoxamine, paroxetine, fluoxetine, and sertraline. In a more particular embodiment, the tricyclic antidepressant is selected from the group consisting of amitriptyline, desipramine, doxepin, protriptyline, trimipramine and nortriptyline. In a more particular embodiment, the monoamine oxidase inhibitor is selected from the group consisting of phenelzine and tranylcypromine. In a more particular embodiment the second drug is selected from the group consisting of drugs that act as inhibitors of neuronal reuptake of both serotonin (5-HT) and norepinephrine (NE). In a more particular embodiment, the inhibitor of neuronal reuptake of both serotonin and norepinephrine is venlafaxine and duloxetine.

In another particular embodiment, the method further comprises treating with an agent that may interfere with the actions of amyloid beta on neurons and other brain cells that may contribute to the pathophysiology of a major depressive disorder in humans.

While it is possible for the agent to be administered alone, it is preferable to present it as a pharmaceutical composition. A generally recognized compendium of methods and ingredients of pharmaceutical compositions is Remington's Pharmaceutical Science, 15th ed., Mack Publishing Company, Easton, Pa. The active ingredient may comprise, for topical administration, from 0.001% to 10% w/w, e.g., from 1% to 2% by weight of the composition, although it may comprise as much as 10% w/w but preferably not in excess of 5% w/w and more preferably from 0.1% to 1% w/w of the composition.

Amyloid beta formation may be retarded, or the progression of amyloidosis may be prevented by an agent of the present invention, including but not limited to a synthetic organic molecule, a protein or peptide, an enzyme, a carbohydrate, a nucleic acid, an antisense oligonucleotide, a small or short interfering RNA molecule (siRNA), or an antibody or fragment thereof. In one particular embodiment, the agent can be used to treat a major depressive disorder. In another particular embodiment, and as noted above, the effects of the agent are through its ability to prevent production or generation of amyloid beta from beta amyloid precursor protein (APP), or by increasing the degradation of amyloid beta, or by increasing the clearance of amyloid beta from the brain, or by facilitating the peripheral metabolism and clearance of amyloid beta.

For example, amyloid beta formation could be inhibited by peptides homologous to Abeta (position 17-21) which have a similar degree of hydrophobicity, but also have a very low propensity to adopt a beta-sheet conformation due to the presence of proline residues (anti-beta-sheet peptides or beta-sheet inhibitors) (Soto C, Kindy M S, Baumann M, Frangione B. Biochem, (1996), Biophys Res Commun., September 24; 226(3):672-80). An 11-residue peptide with these characteristics binds to Abeta, inhibits Abeta fibril formation and partially disaggregates preformed fibrils in vitro. Shorter anti-beta-sheet peptides and analogs containing D-amino acids are also able to inhibit Abeta fibrillogenesis. The latter are more resistant to proteolytic degradation and may serve as a starting point to design more efficient peptides derivatives to inhibit amyloidogenesis in vivo.

Alternatively, it has been determined that N-methyl amino acid containing congeners of the hydrophobic "core domain" of Abeta inhibit the fibrillogenesis of full-length Abeta. These peptides also disassemble preformed fibrils of full-length Abeta. A key feature of the inhibitor peptides is that they contain N-methyl amino acids in alternating positions of the sequence. The most potent of these inhibitors, termed Abeta16-22m, has the sequence NH(2)-K(Me-L)V(Me-F)F (Me-A)E-CONH(2) (SEQ ID NO: 6). These inhibitors appear to act by binding to growth sites of Abeta nuclei and/or fibrils and preventing the propagation of the network of hydrogen bonds that is essential for the formation of an extended beta-sheet fibril. (Gordon D J, Sciarretta K L, Meredith S C., (2001), Biochemistry. July 27; 40(28):8237-45). Furthermore, it has been shown that single N-methyl amino acid-containing peptides related to the central hydrophobic region $\beta_{16-20}$ (Lys-Leu-Val-Phe-Phe (SEQ ID NO: 7) of the β-amyloid protein are able to reduce the cytotoxicity of natural $\beta_{1-42}$ in PC12 cell cultures. N-methyl phenylalanine analogs yield statistically significant increments in cell viability (Student's t-test<0.01%) and are nontoxic in the same assay (M. Cruz, J. M. Tusell, D. Grillo-Bosch, F. Albericio, J. Serratosa, F. Rabanal and E. Giralt, (2004), The Journal of Peptide Research, 63(3): 324).

In addition, it has been shown that phenserine, a third generation acetyicholinesterase inhibitor (AChE-inhibitor), has the ability to reduce both beta amyloid precursor protein (APP) and beta amyloid peptide (amyloid-beta) formation in the brain Other investigators have reported that injection of animals with low molecular weight heparins (enoxaprin and dalteparin) demonstrated a reduction in amyloid beta deposition. Moreover, these compounds were capable of arresting the progression of amyloid beta deposits and amyloid beta peptide fibril formation by impeding the structural changes necessary for fibril formation. Not only was amyloid beta progression retarded, but these molecules enhanced the clearance of established amyloid beta fibrils (Zhu, H. et al. (2001), Mol. Med. 7(8):517-522).

Furthermore, it has been shown that monoclonal antibodies are capable of inhibiting in vitro fibrillar aggregation of the Alzheimer beta-amyloid peptide (Solomon B, et al., (1996), Proc Natl Acad Sci U S A, 93(1):452-5). In one study, two monoclonal antibodies (mAbs), AMY-33 and 6F/3D, were raised against beta-amyloid fragments spanning amino acid residues 1-28 and 8-17 of the beta-amyloid peptide chain, respectively. In vitro aggregation of beta-amyloid peptide was induced by incubation for 3 hours at 37° C. and monitored by ELISA, negative staining electron microscopy, and fluorimetric studies. The investigators found that the monoclonal antibodies prevented the aggregation of beta-amyloid peptide. Moreover, the inhibitory effect appeared to be related to the localization of the antibody-binding sites and the nature of the aggregating agents (Solomon B, et al., (1996), Proc Natl Acad Sci U S A, 93(1):452-5).

It may also be possible to prevent the effects of amyloid beta by administering an agent that effects a regulatory element necessary for its expression. Alternatively, the effects of amyloid beta in a major depressive disorder may be addressed by taking into account the effects of abeta in the inflammatory process. For example, studies by Suo Z. et al suggest that beta-amyloid (Abeta)-induced inflammatory reactions may partially drive the pathogenesis of Alzheimer's disease (AD) and in cerebral amyloid angiopathy (CAA). To evaluate the roles of Abeta in the inflammatory processes in vascular tissues, they tested the ability of Abeta to trigger inflammatory responses in cultured human vascular cells. They found that stimulation with Abeta dose-dependently increased the expression of CD40, and secretion of interferon-gamma (IFN-gamma) and interleukin-1beta (IL-1beta) in endothelial cells. Abeta also induced expression of IFN-gamma receptor (IFN-gammaR) both in endothelial and smooth muscle cells. Characterization of the Abeta-induced inflammatory responses in the vascular cells showed that the ligation of CD40 further increased cytokine production and/or the expression of IFN-gammaR. Moreover, IL-1beta and IFN-gamma synergistically increased the Abeta-induced expression of CD40 and IFN-gammaR. They also found that Abeta induced expression of adhesion molecules, and that cytokine production and interaction of CD40-CD40 ligand (CD40L) further increased the Abeta-induced expression of adhesion molecules in these same cells. These results suggest that Abeta can function as an inflammatory stimulator to activate vascular cells and induces an auto-amplified inflammatory molecular cascade, through interactions among adhesion molecules, CD40-CD40L and cytokines. Additionally, Abeta1-42, the more pathologic form of Abeta, induces much stronger effects in endothelial cells than in smooth muscle cells, while the reverse is true for Abeta1-40. Collectively, these findings support the hypothesis that the Abeta-induced inflammatory responses in vascular cells may play a significant role in the pathogenesis of CAA and AD (Suo et al., (1998), Brain Res, 807(1-2): 110-7).

Studies have also focused on a means of enhancing the degradation and clearance of Abeta. Studies by Qiu et al. have shown increased degradation of amyloid beta protein by a metalloprotease secreted by microglia. Such a metalloprotease was identified in a microglial cell line, BV-2 (Qiu, W Q et al. (1997), J. Biol. Chem. 272(10):6641-6). Substrate analysis revealed that the enzyme responsible for the degradation of $Abeta_{1-40}$ and $Abeta_{1-42}$ was a non-matrix metalloprotease. Thus, it may be possible to develop novel therapeutics that act to enhance the activity of this enzyme or to identify other enzymes that act in a similar manner to degrade the amyloid beta proteins, or alternatively, to develop a means of directing specific enzymes with such amyloid beta degrading activity to the site where needed.

Another enzyme, neprilysin, has been shown to be a major Abeta degrading enzyme in vivo. Studies by Hama, et al. investigated whether or not manipulation of neprilysin activity in the brain would be an effective strategy for regulating Abeta levels. Neprilysin was expressed in primary cortical neurons using a Sindbis viral vector and the effect on Abeta metabolism was examined. The investigators showed that the corresponding recombinant protein, expressed in the cell bodies and processes, exhibited thiorphan-sensitive endopeptidase activity, whereas a mutant neprilysin with an amino acid substitution in the active site did not show any such activity. Expression of the wild-type neprilysin, but not the mutant, resulted in a dose-dependent decrease in both the Abeta40 and 42 levels in the culture media (Hama E. et al. (2001), Journal of Biochemistry, Vol 130, Issue 6: 721-726). Moreover, neprilysin expression also resulted in reducing cell-associated Abeta, which could be more neurotoxic than extracellular Abeta. These results indicate that the manipulation of neprilysin activity ip neurons, the major source of Abeta in the brain, would be a relevant strategy for controlling the Abeta levels and thus the Abeta-associated pathology in brain tissues. In the matter of the present invention, such a strategy could be used to treat a major depressive disorder associated with elevated levels of Abeta peptides.

Studies have also shown that endothelin converting enzyme (ECE) has been shown to play a fundamental role in amyloid metabolic pathways. A published study (Journal of Biological Chemistry: 276(27):24540-8, 2001) reported that both ECE-1a and ECE-1b activation reduced the intracellular generation of Abeta40 and Abeta42, and that ECE-1a may also be able to degrade preexisting protein. The development of strategies able to stimulate or over-express ECE could offer a novel therapy of treating a major depressive disorder characterized by elevated levels of Abeta40 and Abeta42.

Furthermore, it has been shown that a modest increase in astroglial TGF-beta 1 production in aged transgenic mice expressing the human beta-amyloid precursor protein (hAPP) results in a three-fold reduction in the number of parenchymal amyloid plaques, a 50% reduction in the overall Abeta load in the hippocampus and neocortex, and a decrease in the number of dystrophic neuritis (Wyss-Coray T, et al. (2001) Nat Med. 7(5):612-8). These investigators found that in mice expressing hAPP and TGF-beta1, Abeta accumulated substantially in cerebral blood vessels, but not in parenchymal plaques. Furthermore, in human cases of AD, Abeta immunoreactivity associated with parenchymal plaques was inversely correlated with Abeta in blood vessels and cortical TGF-beta1 mRNA levels. The reduction of parenchymal plaques in hAPP/TGF-beta1 mice was associated with a strong activation of microglia and an increase in inflammatory mediators. Recombinant TGF-beta1 stimulated Abeta clearance in microglial cell cultures. These results demonstrate that TGF-beta1 is an important modifier of amyloid beta deposition in vivo and indicate that TGF-beta1 might promote microglial processes that inhibit the accumulation of Abeta in the brain parenchyma. Accordingly, agents that modulate TGF-beta activity may prove useful to treat major depressive disorders by virtue of their effect on Abeta deposition and/or clearance.

In studies related to the role of amyloid beta in Alzheimer's disease, several groups are exploring the possibility that Abeta-based vaccines can help the brain in Alzheimer's patients by increasing its clearance. Work by Lemere et al. demonstrated that vaccinating monkeys with synthetic amyloid beta peptide enhanced the clearance of amyloid beta protein from the brain and into the blood. In this study, five aged Caribbean vervet monkeys were given eight injections of the amyloid beta peptide over a period of nine-months. Five control monkeys did not receive the treatment. The investigators found that all of the immunized monkeys made antibodies to amyloid beta peptide. These antibodies were found in blood and, in lower amounts, in cerebrospinal fluid (CSF). More importantly, the investigators found that between 22 and 42 days after immunization, levels of amyloid beta protein dropped in the CSF and increased in the blood and no plaques were found in the immunized animals. These findings suggest that the antibodies bound to amyloid beta protein and increased its slow release from the CSF to the blood for clearance. One possible drawback to this approach is the finding that foreign beta-amyloid could have unwanted consequences, such as contributing to the death of brain cells or triggering harmful immune system responses. One possible concern is the induction of an inflammatory response in the brain. Thus, it may be necessary to administer other anti-inflammatory compounds at the time of vaccination. The present invention provides for such combination therapies.

One alternative is to find nontoxic molecules that will boost the clearance of beta-amyloid without inducing an inflammatory response. Agadjanyan et al. have found several molecules that mimic beta-amyloid (termed "mimotopes") in mice, and they are now looking for corresponding mimotopes in humans. Future studies by this group will concentrate on identification of beta-amyloid mimotopes in the blood from patients with Alzheimer's disease. These molecules will then be tested in a mouse model of Alzheimer's disease to determine whether vaccination with human mimotopes can reduce mouse brain levels of beta-amyloid and reverse memory deficits, without side effects.

Any of the above agents, whether they are small organic molecules, enzymes, peptides or antibodies, which prevent the production or generation of Abeta through cleavage of APP, or aggregation of amyloid beta fibrils, or promote the degradation and/or clearance of amyloid beta peptides, may be useful for treatment of a major depressive disorder. Such agents may be used alone, or in combination with other therapies such as anti-inflammatories or pain medications or other standard treatments for depression, such as those noted herein. These other therapies may be administered concurrently, or may be given prior to, or after, the agents described above.

Pharmaceutical Compositions

Another aspect of the invention provides for pharmaceutical compositions for the treatment of a major depressive disorder. The pharmaceutical composition comprises an agent that prevents the production or generation of amyloid beta through cleavage of APP, such as an inhibitor of gamma or beta secretase, and a pharmaceutically acceptable carrier, or an agent that prevents aggregation of amyloid beta fibrils and deposition in cerebral parenchymal tissues and blood vessels, or by preventing the formation of oligomeric forms of Abeta, $Abeta_{1-40}$ or $Abeta_{1-42}$, or an agent that increases the degradation of amyloid beta and a pharmaceutically acceptable carrier, or an agent that increases the clearance of amyloid beta from the brain and a pharmaceutically acceptable carrier, or an agent that facilitates the metabolism of amyloid beta and a pharmaceutically acceptable carrier. The pharmaceutical compositions may be formulated for oral delivery or parenteral delivery. Furthermore, the pharmaceutical compositions are formulated for delivery by a route selected from the group consisting of intravenous, intramuscular, oral, subcutaneous, intrathecal, intracranial and intraventricular. In a particular embodiment, the amyloid beta is amyloid $beta_{1-40}$ or amyloid $beta_{1-42}$.

The compositions for parenteral administration will commonly comprise a solution of any of the agents described above, including an antibody or fragment thereof or a protein or small organic molecule of the invention or a cocktail thereof dissolved in an acceptable carrier, preferably an aqueous carrier. A variety of aqueous carriers may be employed, e.g., water, buffered water, 0.4% saline, 0.3% glycine, and the like. These solutions are sterile and generally free of particulate matter. These solutions may be sterilized by conventional, well-known sterilization techniques. The compositions may contain pharmaceutically acceptable auxiliary substances as required to approximate physiological conditions such as pH adjusting and buffering agents, etc. The concentration of the agent of the invention in such pharmaceutical compositions may vary widely, i.e., from less than about 0.5%, usually at or at least about 1% to as much as 15 or 20% by weight, and will be selected primarily based on fluid volumes, viscosities, etc., according to the particular mode of administration selected.

Thus, a pharmaceutical composition of the invention for intramuscular injection could be prepared to contain 1 ml sterile buffered water, and 50 mg of agent of the invention. Similarly, a pharmaceutical composition of the invention for intravenous infusion could be made up to contain 250 ml of sterile Ringer's solution, and 150 mg of the agent of the invention. Actual methods for preparing parenterally administrable compositions are well-known or will be apparent to those skilled in the art, and are described in more detail in, e.g., Remington's Pharmaceutical Science, 15th ed., Mack Publishing Company, Easton, Pa.

The agent of the invention may be lyophilized for storage and reconstituted in a suitable carrier prior to use.

The pharmaceutical composition of the invention may be administered for prophylactic and/or therapeutic treatments. In therapeutic application, compositions are administered to a subject already suffering from a major depressive disorder, in an amount sufficient to cure or at least partially arrest the disorder and its complications. In prophylactic applications, compositions containing the present agents are administered to a subject not already in a disease state but one that may be predisposed to a depressive disorder to enhance the subject's resistance to such disorder.

It will be recognized by one of skill in the art that the optimal quantity and spacing of individual dosages of an agent of the invention will be determined by the nature and extent of the depressive disorder being treated, the form, route and site of administration, and the particular animal being treated, and that such optimums may be determined by conventional techniques. It will also be appreciated by one of skill in the art that the optimal course of treatment, i.e., the number of doses of an agent of the invention given per day for a defined number of days, may be ascertained by those skilled in the art using conventional course of treatment determination tests.

Administration of the Pharmaceutical Compositions

According to the present invention, a therapeutic composition, e.g., an inhibitor of amyloid beta production or generation through cleavage of amyloid precursor protein (APP), an inhibitor of amyloid beta aggregation into fibrils, an enhancer of amyloid beta clearance from the brain, an enhancer of amyloid beta degradation, or an agent that interferes with the neurotoxic effects of amyloid beta, and a pharmaceutically acceptable carrier of the invention or an agent such as a small organic molecule or an antibody that performs one of these functions, may be introduced orally or parenterally, e.g. intramuscularly, intravenously, subcutaneously, transmucosally, or nasally. Alternatively, administration is by intracranial, intrathecal or intraventricular administration. In addition, the therapeutic composition can be placed (e.g., injected) into the bloodstream after coupling the agent to a carrier that will allow the agent-carrier complex to cross the blood-brain barrier.

In a preferred aspect, the agent of the present invention can cross cellular or nuclear membranes, which would allow for intravenous or oral administration. Strategies are available for such crossing, including but not limited to, increasing the hydrophobic nature of a molecule; introducing the molecule as a conjugate to a carrier, such as a ligand to a specific receptor, targeted to a receptor; and the like.

The present invention also provides for conjugating targeting molecules to the agent of the invention. "Targeting molecule" as used herein shall mean a molecule which, when administered in vivo, localizes to desired location(s). In various embodiments, the targeting molecule can be a peptide or protein, antibody, lectin, carbohydrate, or steroid. In one embodiment, the targeting molecule is a peptide ligand of a receptor on the target cell. In a specific embodiment, the targeting molecule is an antibody. Preferably, the targeting molecule is a monoclonal antibody. In one embodiment, to facilitate crosslinking, the antibody can be reduced to two heavy and light chain heterodimers, or the F(ab')$_2$ fragment can be reduced, and crosslinked to the agent via a reduced sulfhydryl.

Antibodies for use as targeting molecule are specific for a cell surface antigen. In one embodiment, the antigen is a receptor. For example, an antibody specific for a receptor on a neuronal cell can be used. This invention further provides for the use of other targeting molecules, such as lectins, carbohydrates, proteins and steroids.

In another embodiment, the therapeutic compound can be delivered in a vesicle, in particular a liposome (see Langer, (1990) *Science*, 249:1527-1533; Treat et al., (1989) in *Liposomes in the Therapy of Infectious Disease and Cancer*, Lopez-Berestein and Fidler (eds.), Liss: New York, pp. 353-365; Lopez-Berestein, ibid., pp. 317-327; see generally ibid.).

In yet another embodiment, the therapeutic compound can be delivered in a controlled release system. For example, the agent may be administered using intravenous infusion, an implantable osmotic pump, a transdermal patch, liposomes, or other modes of administration. In one embodiment, a pump may be used (see Langer (1990) supra; Sefton, (1987) *CRC Crit. Ref. Biomed. Eng.*, 14:201; Buchwald et al., (1980) *Surgery*, 88:507; Saudek et al., (1989) *N. Engl. J. Med.*, 321: 574). In another embodiment, polymeric materials can be used (see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, (1983) *J. Macromol. Sci. Rev. Macromol. Chem.*, 23:61; see also Levy et al., (1985) *Science*, 228:190; During et al., (1989) *Ann. Neurol.*, 25:351; Howard et al., (1989) *J. Neurosurg.*, 71:105). In yet another embodiment, a controlled release system can be placed in proximity of the therapeutic target, i.e., the brain, thus requiring only a fraction of the systemic dose (see, e.g., Goodson, in *Medical Applications of Controlled Release*, supra, vol. 2, pp. 115-138 (1984)).

Screening Assays for Identification of Novel Agents for Treating Major Depressive Disorder A still further aspect of the invention relates to screening assays to identify agents which inhibit the production or generation of Abeta by cleavage of APP or the aggregation of amyloid beta fibrils or to enhance the degradation or clearance of Abeta. The invention encompasses both in vivo and in vitro assays to screen small molecules, compounds, recombinant proteins, peptides, enzymes, nucleic acids, antibodies, etc. which exhibit any of the above activities.

In a preferred embodiment, the binding of the agent is determined through the use of competitive binding assays. The competitor is an antibody of the invention known to bind to amyloid beta protein, including Abeta$_{40}$ and Abeta$_{42}$, or fragments thereof. Competitive screening assays may be done by combining the amyloid beta protein and an antibody of the invention in a first sample. A second sample comprises a test agent, amyloid beta and an antibody of the invention. The binding of the antibody is determined for both samples, and a change, or difference in binding between the two samples indicates the presence of a test agent capable of binding to amyloid beta and potentially modulating its conformational structure and/or activity. That is, if the binding of the antibody is different in the second sample relative to the first sample, the test agent is capable of binding to amyloid beta protein. Similar designs that utilize antibodies of this invention for the identification of non-antibody compounds that bind to amyloid beta are obvious to those skilled in the art.

One variation provides that the agent is labeled. Either the agent, or the competitor, or both, is added first to amyloid beta protein for a time sufficient to allow binding. Incubations may be performed at any temperature which facilitates optimal activity, typically between 4° C. and 40° C. Incubation periods are selected for optimum activity, but may also be optimized to facilitate rapid high-throughput screening. Typically between 0.1 and 1 hour will be sufficient. Excess reagent is generally removed or washed away. The second component is then added, and the presence or absence of the labeled component is followed, to indicate binding.

It is preferred that the competitor is added first, followed by the test agent. Displacement of the competing antibody of this invention is an indication that the test agent is binding to amyloid beta protein and thus is capable of binding to, and potentially modulating, the conformational structure and/or activity of amyloid beta protein. In this reaction either component may be labeled. Thus, for example, if the competitor is labeled, the presence of label in the wash solution indicates displacement by the agent. Alternatively, if the test agent is labeled, the presence of the label on the support indicates displacement.

Alternatively, the test agent is added first, with incubation and washing, followed by the competitor. The absence of binding by the competitor may indicate the test agent is bound to amyloid beta protein with a higher affinity. Thus, if the agent is labeled, the presence of the label on the support, coupled with a lack of competitor binding, may indicate the test agent is capable of binding to amyloid beta protein.

The agents encompass numerous chemical classes, though typically they are organic molecules, preferably small organic compounds having a molecular weight of more than 100 and less than about 3,500 daltons. Agents comprise functional groups necessary for structural interaction with proteins, particularly hydrogen bonding, and typically include at least an amine, carbonyl, hydroxyl or carboxyl group, preferably at least two of the functional chemical groups. The agents often comprise cyclical carbon or heterocyclic structures and/or aromatic or polyaromatic structures substituted with one or more of the above functional groups. Agents may also be found among biomolecules including peptides, saccharides, fatty acids, steroids, purines, pyrimidines, derivatives, structural analogs or combinations thereof.

Agents are obtained from a wide variety of sources including libraries of synthetic or natural compounds.

Alternatively, the antibodies of this invention may be used for the design and synthesis of either peptide or non-peptide compounds (mimetics) that specifically bind to amyloid beta.

The assays provided use amyloid beta protein, Abeta$_{40}$, Abeta$_{42}$, or fragments of any of these molecules. In addition, the assays described herein may use either isolated amyloid beta, Abeta$_{40}$, Abeta$_{42}$, or fragments thereof or cells expressing these molecules or animal models that express these molecules.

A variety of other reagents may be included in the screening assays. These include reagents like salts, neutral proteins, e.g. albumin, detergents, etc. which may be used to facilitate optimal protein-protein binding and/or reduce non-specific or background interactions. Also, reagents that otherwise improve the efficiency of the assay, such as protease inhibitors, nuclease inhibitors, anti-microbial agents, and the like may be used. The mixture of components may be added in any order that provides for the requisite binding.

The methods of the invention are used to identify compounds that inhibit the production or generation of Abeta through cleavage of APP, such as a gamma or beta secretase inhibitor, or the aggregation of amyloid beta fibrils, or which enhance the degradation or clearance of Abeta, and are therefore useful in the treatment of disorders, diseases or conditions attributed to elevated levels of amyloid beta, in particular, Abeta$_{42}$ or fragments thereof. In the present invention, such elevated levels of amyloid beta have been found in the plasma of patients suffering from a major depressive disorder and have been attributed to development and/or progression of such disorders. A depressed mood is a common feature not only in Major Depressive Episodes/Disorders, but in other mood disorders such as Dysthymic Disorder or Bipolar Disorder. Accordingly, major depressive disorders which can be treated by the methods and compositions provided herein include, but are not limited to, Major Depressive Episodes and/or Disorders. To the extent that other mood disorders such as Dysthymic Disorder, bipolar disorders, and the like, may share abnormal or elevated Abeta levels, in particular Abeta$_{1-42}$ such as has been observed in Major Depressive Episodes/Disorders, then therapies that are applicable to Major Depressive Episodes/Disorders as related to the reduction in Abeta may also be applicable to treatment of these disorders. Since an increase in Abeta may interfere with neurotransmitters or with their corresponding signaling systems, which may play a role in other disorders such as anxiety or Schizophrenia, then therapies as defined herein to lower levels of Abeta peptides may be useful for the treatment of these disorders, or the depression associated with these disorders, as well. Furthermore, the use of agents as described herein to treat depressive episodes or disorders may be contemplated as stand-alone therapy or may be used as adjunct therapy with other standard forms of therapy or treatment regimens for depression. It is not yet clear that elevated plasma Abeta levels, eg. A$\beta_{42}$, are related to elevations in brain A$\beta_{42}$ levels in humans. However, there are a number of preclinical studies, which provide strong evidence that brain and plasma levels are in a dynamic equilibrium (Bading, J. R., Yamada, S., Mackic, J. B., Kirkman, L., Mille, C., Caler, M., Ghiso, J., Frangione, B., and Zlokovic, B. V; Drug Target, (2002), 10: 359-368; Poduslo, J. F., Curran, G. L., Sanya, B., and Selkoe, D. J., (1999), Neurobiol Dis. 6: 190-199; Zlokovic, B. V., Martel, C. L., Mackic, J. B., Matsubara, E., Wisniewski, T., McComb, J. G., Frangione, B., and Ghiso, J., (1994), Biochem Biophys Res Commun. 205: 1431-1437; Tanzi R E, Moir R D, Wagner S L., (2004), Neuron. 43: 605-608). This may suggest that a treatment that reduces peripheral levels of Abeta, eg. A$\beta_{42}$, might also lower the brain levels of Abeta, eg. A$\beta_{42}$, as well.

In the same manner that a small organic molecule or enzyme or mimotope having the desired activity and characteristics noted above, e.g. a molecule that blocks the production or generation of Abeta, or blocks the aggregation of amyloid beta, or enhances its degradation or clearance, may be administered to treat a major depressive disorder, so may an antibody specific for amyloid beta, Abeta$_{40}$, Abeta$_{42}$ or fragments thereof be administered to treat a major depressive disorder. Accordingly, a further aspect of the invention provides methods for treating a major depressive disorder by administering to a subject with such disorder an antibody which binds to and therefore blocks the functionally significant region(s) of amyloid beta, Abeta$_{40}$ and Abeta$_{42}$ or fragments thereof. As one of skill in the art may appreciate, the pharmaceutical compositions comprising the antibody and a pharmaceutically acceptable carrier, as well as the route of administration of such pharmaceutical compositions, would be similar to those provided above for the other agents of this invention. The optimal quantity and spacing of individual dosages of an agent of the invention will be determined by the nature of the agent, the nature and extent of the disorder being treated, the form, route and site of administration, and the particular animal being treated. Such optimums may be determined by conventional techniques of monitoring clinical depression.

EXAMPLES

The following examples are put forth so as to provide those of ordinary skill in the art with a complete disclosure and description of how to assess the levels of amyloid beta in a population of clinically depressed patients, and are not intended to limit the scope of what the inventors regard as their invention.

Example 1

Elevation in Plasma Abeta42 in Geriatric Depression

Materials and Methods

Participants: Plasma samples were obtained from a subset of LLMD patients (N=47; 36 females) who had participated in a double blind randomized comparison of nortriptyline and paroxetine. The clinical characteristics of the LLMD patient samples were previously described (Mulsant, B. H., Pollock, B. G., Nebes, R. D., Miller, M. D., Little, J. T., Stack, J., Houck, P. R., Bensasi, S., Mazumdar, S., and Reynolds, C. F. 3$^{rd}$ (1999), A double-blind randomized comparison of nortriptyline and paroxetine in the treatment of late-life depression: 6-week outcome. *J Clin Psychiatry* 60 Suppl 20:16-20) and are briefly summarized here. The sample included inpatients and outpatients with LLMD and all subjects underwent comprehensive assessments consisting of a psychiatric history and mental status evaluation, social and medical history, physical exam, and laboratory tests. The Structured Clinical Interview for DSM-IV Axis I disorders (SCID-IV), the 17-item Hamilton Rating Scale for Depression (HAM-D, Hamilton, 1960; mean=21.3, sd=4.0), and the Mini-Mental State Examination (MMSE (Folstein, M. F., Folstein, S. E., and McHugh, P. R. (1975), "Mini-mental state". A practical method for grading the cognitive state of patients for the clinician. *J Psychiatr Res* 12:189-198); mean=26.4, sd=3.0) were employed for the evaluation. Other characteristics of these study participants included: age of 60 years or older (age range 67 to 99 years; mean age=80.0, sd=7.4), DMS-IV major depressive episode without psychotic features or history of bipolar or schizoaffective disorder, baseline HAM-D score of 15 or above, MMSE score of 18 or above, no history of alcohol or other substance abuse or dependency during at least the past year, and no specific medical condition contraindicating treatment with either nortriptyline or paroxetine. A subset of these subjects also participated in a neuroimaging MRI study which included, as described elsewhere (Butters, M. A., Whyte, E. M., Nebes, R. D., Begley, A. E., Dew, M. A., Mulsant, B. H., Zmuda, M. D., Bhalla, R., Meltzer, C. C., Pollock, B. G., Reynolds, C. F. 3rd, and Becker, J. T. (2004), The nature and determinants of neuropsychological functioning in late-life depression. *Arch Gen Psychiatry* 61:587-595), measures of total white matter hyperintensity burden and ventricular atrophy rated on a 10-point scale representing progressive severity (0-9, 9=most severe). Following completion of these evaluations and washout of all psychotropic medications except for lorazepam, subjects participated in a double-blind study in which they were treated with either nortriptyline or paroxetine for 6 weeks.

Plasma samples were also obtained from 35 nondepressed cognitively-intact elderly controls (21 females; age range 62 to 79 years; mean age=69.1, sd=4.4) who had previously participated in a study examining the acute effects of lorazepam (Pomara, N., Willoughby, L., Wesnes, K., et al. (2005), Apolipoprotein E ε-4 allele and lorazepam effects on memory in high-functioning older adults. *Arch Gen Psychiatry*. 2005; 62:209-216). Participants were in good health and free psychiatric disorders as determined by medical history, psychiatric evaluation, physical exam, and laboratory tests. The control subjects were free of cognitive impairment as determined by a comprehensive neurocognitive assessment, including meeting study entry criteria of having an age-corrected Wechsler Memory Scale Memory Quotient of 85 or better, age-corrected Wechsler Adult Intelligence Scale Intelligence Quotient of 85 or better, and a Mini-Mental State Exam score of 28 or better. These control subjects had also subsequently participated in a longitudinal study involving annual cognitive tests, which included the MMSE (mean=29.3, sd=0.72) and were free of depressive disorder/ symptoms, as determined by psychiatric interview and the 21-item HAM-D (mean=0.9, sd=1.6).

Aβ Assays: Plasma $A\beta_{40}$ and $A\beta_{42}$ levels were determined using a previously described method (Mehta, P. D., Dalton, A. J., Mehta, S. P., Kim, K. S., Sersen, E. A., and Wisniewski, H. M. (1998), Increased plasma amyloid beta protein 1-42 levels in Down syndrome. *Neurosci Lett* 241:13-16) involving a combination of monoclonal antibody (mAb) 6E10 (specific to an epitope present on 1-16 amino acid residues of Aβ) and R359 and R306 respectively in a double antibody sandwich ELISA. The detection limit was 9.5 pg/ml for $A\beta_{40}$ and 7 pg/ml for $A\beta_{42}$. The mean of the coefficient of within assay variation was 4.6% for $A\beta_{40}$, and 9.3% for $A_{42}$. The reliability of the assay was tested by assaying 11 plasma samples two times in a period of 30 days ($A\beta_{40}$: r=0.89, P<0.001; $A\beta_{42}$: r=0.87, P<0.001). For the current study, each plasma sample was assayed on two different occasions separated by approximately one week. The averages of the two assays were used in the analyses presented below. Aβ determinations were made simultaneously for all samples within each group. Plasma Aβ levels were determined in samples collected at pre- and post-treatment from the LLMD group.

Platelet Activation Assay: Samples were collected in CTAD vacutainer tubes containing sodium citrate, theophylline, adenosine, and dipyridamole. The first 2 ml of blood were disposed using a pediatric 2 ml Vacutainer and 4 ml of blood will be collected into CTAD tubes, which were inverted several times to mix the blood with anticoagulant agents and placed immediately in an ice-water bath. The tubes rested for 15 minutes on ice and were centrifuged at 2500 RPM for 20 minutes at 2-7° C. PF4 and BTG were measured in platelet-poor plasma samples using commercial enzyme immunoassay kits (American Bioproducts).

Statistical Analyses: Independent samples t-tests were performed to compare plasma $A\beta_{40}$ levels, $A\beta_{42}$ levels, and the $A\beta_{40}$ ratio in LLMD and control groups. Nonparametric analyses (Mann-Whitney-U tests) were applied when group sample sizes were substantially unbalanced. Correlational analyses were performed using Pearson's product moment correlation coefficients. An alpha level of 0.05 was used for all tests. This was an exploratory study with a priori hypotheses and hence we did not perform adjustments for multiple comparisons. Readers should view the p-values<0.05 in this light rather than as definitive evidence of significance.

Results

Figure 2:
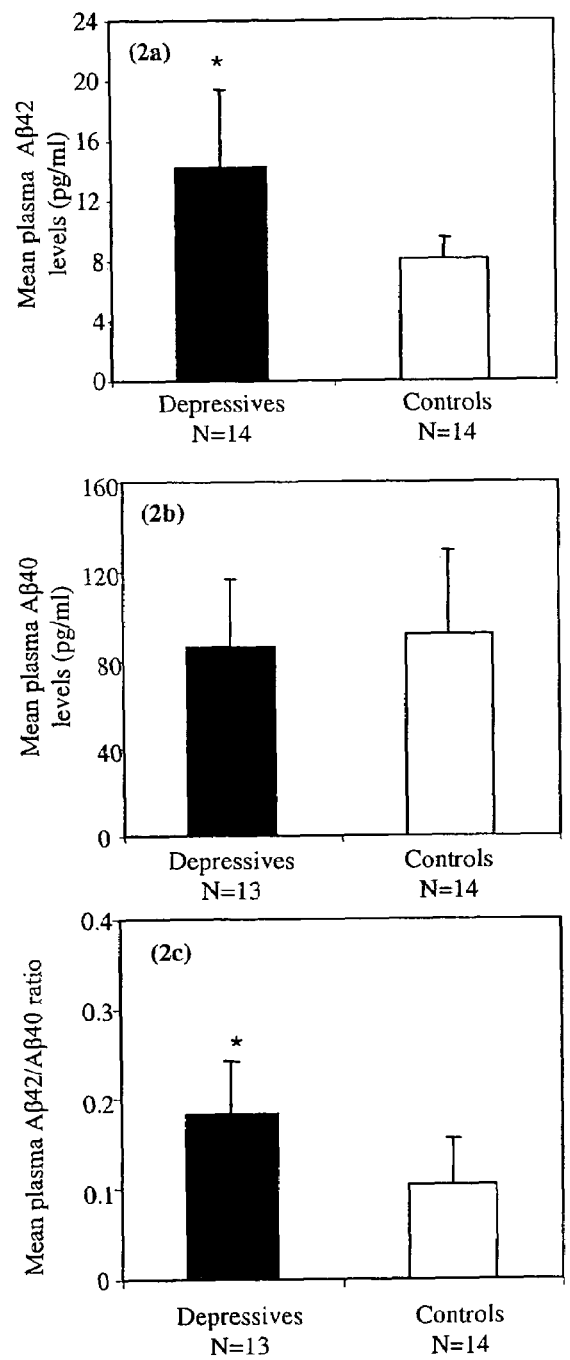
FIG. 2. Mean plasma Aβ$_{42}$ levels (2a), Aβ$_{40}$ levels (2b), and Aβ$_{42}$/Aβ$_{40}$ ratio (2c) in age- and gender-matched samples of cognitively intact elderly depressives and controls. Error bars represent standard deviations.

Plasma Abeta Levels in Depressives and Controls: Baseline (pre-treatment) plasma $A\beta_{40}$ and $A\beta_{42}$ levels were available for 45 and 42 LLMD subjects, respectively, and for all 35 nondepressed controls. As shown in FIG. 1, plasma $A\beta_{42}$ levels were elevated by approximately 30% in the depressives compared to controls [t (75)=2.51, P=0.014] and plasma $A\beta_{40}$ levels did not differ between the groups [t (78)<1]. Additionally, the $A\beta_{42/40}$ ratio was higher in LLMD subjects compared to controls [t (73)=3.43, P=0.001]. Due to group differences in age and MMSE scores (P<0.05), we also repeated the analyses on a subset of controls and LLMD subjects who had an MMSE score of 25 or better and were matched on age (±2 years) and gender while blinded to Aβ levels. The resulting matched samples included 14 (11 females) LLMD (mean age=72.1, sd=3:6; mean HAM-D=21.4, sd=4.2; mean MMSE=27.8, sd=1.8) and 14 controls (mean age=71.6, sd=3.3; mean HAM-D=0.4, sd=1.3; mean MMSE=29.1, sd=0.8). As shown in FIG. 2, analyses performed on the age- and sex-matched subgroups produced results similar to the overall group analyses, with higher $A\beta_{42}$ levels [t(26)=4.30, P<0.001] and $A\beta_{42/40}$ ratio [t(25)=3.77, P=0.001] in LLMD compared to controls and no group differences in $A\beta_{40}$ levels.

Figure 3:
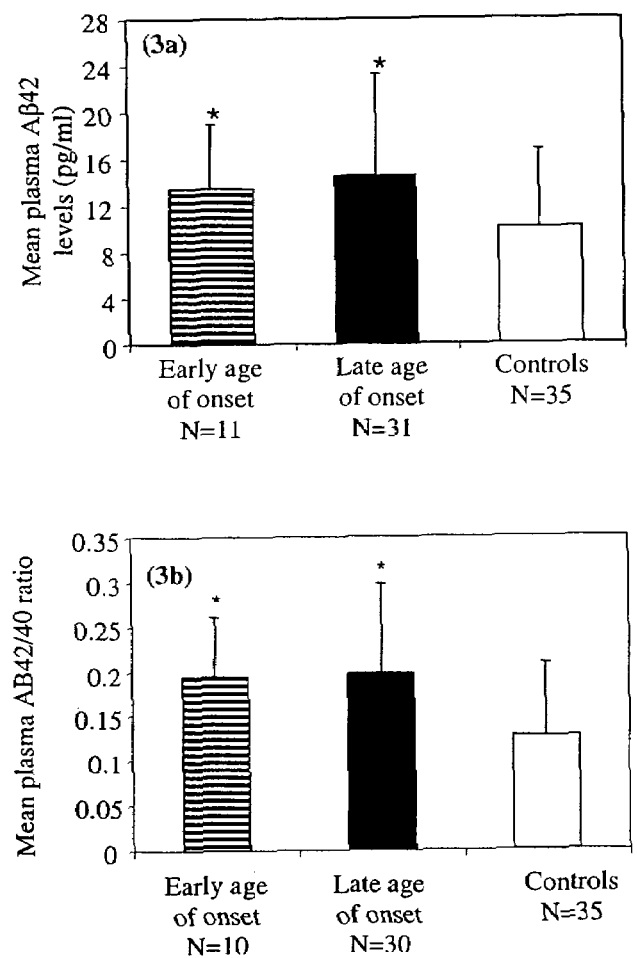
FIG. 3. Mean plasma Aβ$_{42}$ levels (2a) and Aβ$_{42}$/Aβ$_{40}$ ratio (2b) in elderly depressives whose age of onset of first depressive episode was early (<60 years) or late (>=60 years) and in controls. Error bars represent standard deviations.

Age of Onset: We also examined the effects of age of onset of first depressive episode (early age of onset<60 years old and late age of onset> or =60 years old). Due to considerable sample size differences between the groups (early-onset n=11, late-onset n=36, controls n=35), nonparametric analyses were applied (Mann Whitney U). As shown in FIG. 3, higher plasma $A\beta_{42}$ levels and $A\beta_{42/40}$ ratio were observed in depressives relative to controls regardless of whether age of onset of first depressive episode was early (U=76, P=0.002 and U=70, P=0.004, respectively) or late (U=300.5, P=0.001 and U=228, P<0.001, respectively).

Figure 4:
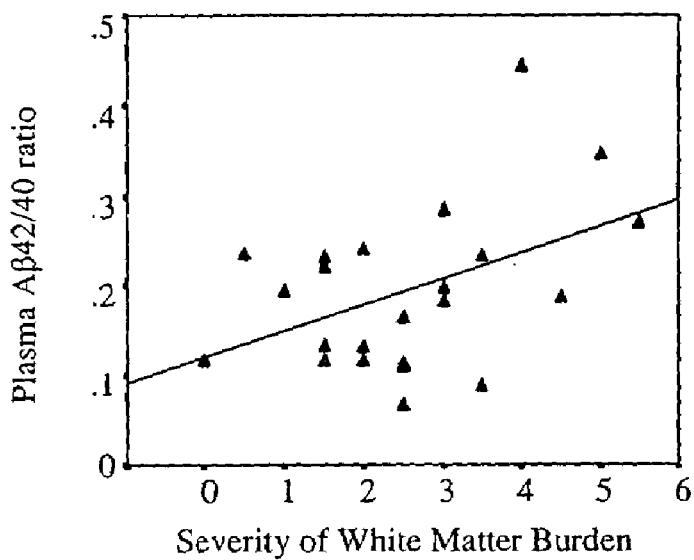
FIG. 4. The relationship between baseline plasma Aβ$_{42/40}$ ratio and a measure of severity of white matter burden.

White Matter Hyperintensities: Pearson's correlation analyses indicated that higher pretreatment $A\beta_{42/40}$ ratio was associated with increased severity of total white matter hyperintensity burden (r=0.44, n=24, P=0.03; FIG. 4) in LLMD subjects, and this relationship was evident even after controlling for MMSE and age (r=0.44, df=20, P<0.04). No significant relationship was detected between Aβ levels and two measures of brain atrophy (i.e., ventricular and sulcal atrophy).

Figure 5:
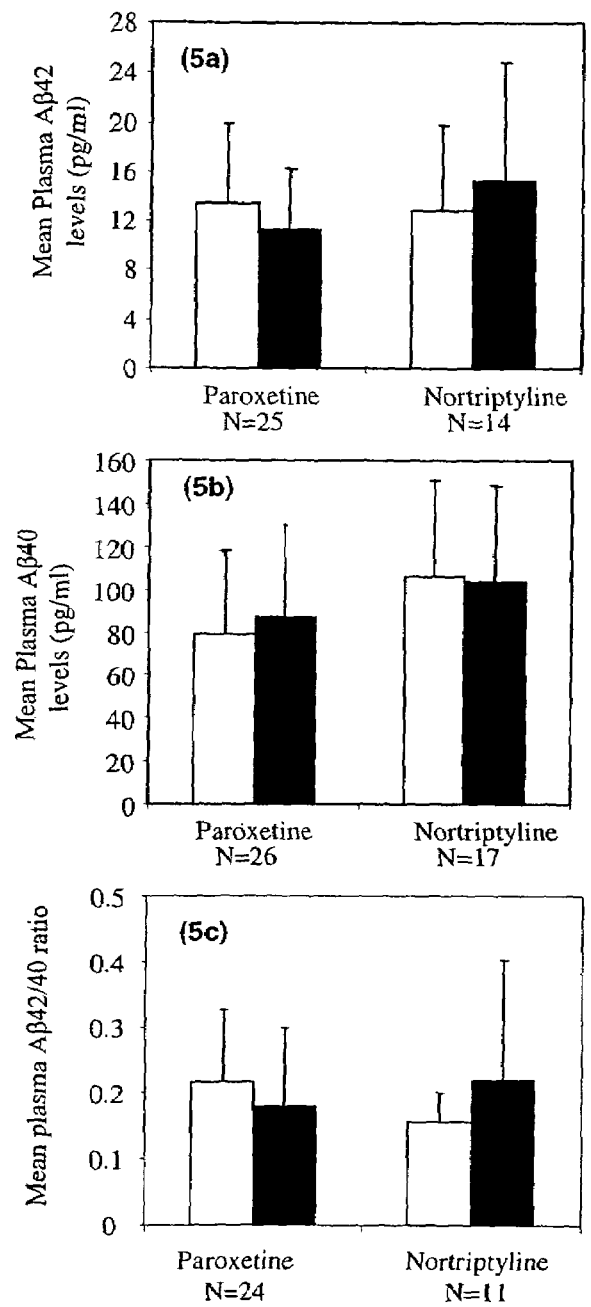
FIG. 5. Mean plasma Aβ$_{42}$ levels (4a), Aβ$_{40}$ levels (4b), and Aβ$_{42/40}$ ratio (4c) in elderly depressives with both pre-treatment (white bars) and post-treatment (black bars) with 6 weeks of paroxetine or nortriptyline values available (bars represent standard deviations).

Effects of 6-Weeks Antidepressant Treatment: Differences in plasma levels of $A\beta_{40}$, $A\beta_{42}$, and $A\beta_{42/40}$ ratio in LLMD subjects measured before and after treatment with paroxetine or nortriptyline for 6 weeks were not detected. There were also no significant differences between antidepressant treatments in plasma levels of $A\beta_{40}$, $A\beta_{42}$, and $A\beta_{42/40}$ ratio detected at each sampling time (FIG. 5). Similar results were found after MMSE and age were entered into the model as covariates.

Relationships Between Indices of Platelet Activation and Plasma Aβ Levels: Pearson correlational analyses performed in elderly depressives revealed no significant relationship between pre-treatment plasma PF4 levels and pre-treatment plasma $A\beta_{40}$ levels (n=44, r=0.04, P=0.79), $A\beta_{42}$ levels (r=0.002, n=41, P=0.99), or $A\beta_{42}$ (r=0.03, n=39, P=0.85). Similarly, no relationship was found between pre-treatment plasma β-TG levels and pre-treatment plasma $A\beta_{40}$ levels (r=0.06, n=36, P=0.71), $A\beta_{42}$ levels (r=0.09, n=33, P=0.63), or $A\beta_{42/40}$ ratio (r=0.11, n=31, P=0.56). These relationships remained nonsignificant even after controlling for age and MMSE.

Figure 6:
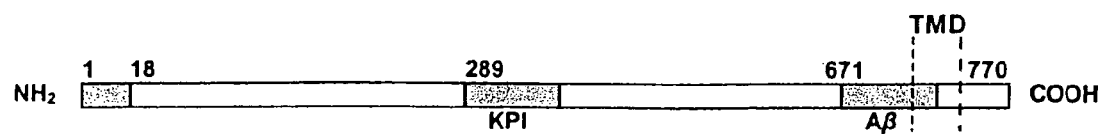
FIG. 6 shows a schematic structure of the amyloid beta precursor protein (APP) consisting of 770 amino acid residues, with the amyloid beta peptides (Aβ$_{1-40}$ and Aβ$_{1-42}$) embedded in its structure. Sequential proteolytic cleavage by gamma and beta secretase leads to Aβ formation. KPI: Kunitz type serine protease inhibitor motif; TMD: transmembrane domain.

FIG. 6 shows a schematic representation of amyloid beta protein precursor, and FIG. 7 shows the sequence of the Aβ peptides 1-39, 1-40 and 1-42 (SEQ ID NO: 8).

Summary and Discussion

To our knowledge, this is the first report of elevations in plasma $A\beta_{42}$ levels and the $A\beta_{42/40}$ ratio in elderly individuals with late-life major depression (LLMD). Plasma $A\beta_{42}$ levels were, on average, 30% greater in elderly with LLMD compared to controls. The elevation in plasma $A\beta_{42}$ in LLMD was even greater when the analyses were performed on the age- and gender-matched groups. Additionally, the $A\beta_{42/40}$ ratio, which has been found to be a better discriminator of AD from nondemented elderly than $A\beta_{42}$ alone (Lewczuk, P., Esselmann, H., Otto, M., Maler, J. M., Henkel, A. W., Henkel, M. K., Eikenberg, O., Antz, C., Krause, W. R., Reulbach, U., Kornhuber, J., and Wiltfang, J. (2004), Neurochemical diagnosis of Alzheimer's dementia by CSF Abeta$_{42}$, Abeta$_{42}$/Abeta$_{40}$ ratio and total tau. Neurobiol Aging 25:273-281) and to be increased in conjunction with familial AD-linked mutations (Borchelt, D. R., Thinakaran, G., Eckman, C. B., Lee, M. K., Davenport, F., Ratovitsky, T., Prada, C. M., Kim, G., Seekins, S., Yager, D., Slunt, H. H., Wang, R., Seeger, M., Levey, A. I., Gandy, S. E., Copeland, N. G., Jenkins, N. A., Price, D. L., Younkin, S. G., and Sisodia, S. S. (1996), Familial Alzheimer's disease-linked presenilin 1 variants elevate Abeta$_{1-42/1-40}$ ratio in vitro and in vivo. Neuron 17:1005-1013-32; Jankowsky, J. L., Fadale, D. J., Anderson, J., Xu, G. M., Gonzales, V., Jenkins, N. A., Copeland, N. G., Lee, M. K., Younkin, L, H., Wagner, S. L., Younkin, S. G., and Borchelt, D. R. (2004), Mutant presenilins specifically elevate the levels of the 42 residue beta-amyloid peptide in vivo: evidence for augmentation of a 42-specific gamma secretase. Hum Mol Genet 13:159-170), was elevated in depressives relative to controls, both in the overall analyses and in the matched groups analyses, indicating a possible disturbance in $A\beta_{42}$ metabolism and/or clearance in LLMD.

We also found a significant correlation between the $A\beta_{42/40}$ ratio and overall severity of total white matter hyperintensity burden. This finding is generally consistent with another report in a large population of nondepressed elderly in which higher plasma Aβ levels were associated with lacunar infarcts and white matter lesions (van Dijk, E. J., Prins, N. D., Vermeer, S. E., Hofman, A., van Duijn, C. M., Koudstaal, P. J., and Breteler, M. M. (2004), Plasma amyloid beta, apolipoprotein E, lacunar infarcts, and white matter lesions. Ann Neurol 55:570-575). Findings from the current study also complement evidence implicating Aβ in the development of cerebral amyloid angiopathy (Greenberg, S. M., Gurol, M. E., Rosand, J., and Smith E E (2004). Amyloid angiopathy-related vascular cognitive impairment. Stroke 35 Suppl I:2616-2619), which could contribute to the ischemic lesions and cerebrovascular disease that have been etiologically implicated in LLMD (Krishnan, K. R., Taylor, W. D., McQuoid, D. R., MacFall, J. R., Payne, M. E., Provenzale, J. M., and Steffens, D. C. (2004), Clinical characteristics of magnetic resonance imaging-defined subcortical ischemic depression. Biol Psychiatry 55:390-397; Alexopoulos, G. S., Meyers, B. S., Young, R. C., Campbell, S., Silbersweig, D., and Charlson, M. (1997), Vascular depression hypothesis. Arch Gen Psychiatry 54:915-922; Thomas, A. J., O'Brien, J. T., Davis, S., Ballard, C., Barber, R., Kalaria, R. N., and Perry, R. H. (2002), Ischemic basis for deep white matter hyperintensities in major depression: A neuropathological study. Arch Gen Psychiatry 59:785-792). In contrast, we found no significant correlation between plasma Aβ measures and indices of brain atrophy. Given that measures of white matter hyperintensities and brain atrophy are usually intercorrelated, this finding could be related to the small sample size and/or the particular measures of brain atrophy that were used.

Elevated plasma $A\beta_{42}$ levels have been reported in asymptomatic individuals with various APP, PS1, and PS2 mutations (Scheuner, D., Eckman, C., Jensen, M., Song, X., Citron, M., Suzuki, N., Bird, T. D., Hardy, J., Hutton, M., Kukull, W., Larson, E., Levy-Lahad, E., Viitanen, M., Peskind, E., Poorkaj, P., Schellenberg, G., Tanzi, R., Wasco, W., Lannfelt, L., Selkoe, D., and Younkin, S. (1996), Secreted amyloid beta-protein similar to that in the senile plaques of Alzheimer's disease is increased in vivo by the presenilin 1 and 2 and APP mutations linked to familial Alzheimer's disease. Nat Med 2:864-870), which are deterministic for subsequent development of familial AD, as well as, in nondemented individuals with Down's syndrome (Schupf, N., Silverman, W., Zigman, W. B., Zhong, N., Tycko, B., Mehta, P. D., and Mayeux, R. (2001), Elevated plasma amyloid beta-peptide 1-42 and onset of dementia in adults with Down syndrome. Neurosci Lett 301:199-203), a group who will inevitably develop AD with increasing age. As previously stated, large-scale longitudinal studies in the general population, suggest that elevated plasma $A\beta_{42}$ is a significant risk factor for AD in nondemented, non-depressed elderly (Mayeux, R., Tang, M. X., Jacobs, D. M., Manly, J., Bell, K., Merchant, C., Small, S. A., Stern, Y., Wisniewski, H. M., and Mehta, P. D. (1999), Plasma amyloid beta-peptide 1-42 and incipient Alzheimer's disease. Ann Neurol 46:412-416—Mayeux, R., Honig, L. S., Tang, M. X., Manly, J., Stern, Y., Schupf, N., and Mehta, P. D.

(2003), Plasma Abeta$_{40}$ and Abeta$_{42}$ and Alzheimer's disease: relation to age, mortality, and risk. *Neurology* 61:1185-1190). Thus, our finding of elevated plasma Aβ$_{42}$ highlights the need to confirm this result and to determine the relationship of plasma Aβ$_{42}$ with the increased risk for AD and cognitive decline in individuals with LLMD. Additionally, the possible relationship of elevated plasma Aβ$_{42}$ levels to the structural and functional brain abnormalities, which have been reported in elderly depressives and particularly in those with a late age of onset of first depressive episode, need to be studied.

In the study presented here, elevations in plasma Aβ$_{42}$ and the Aβ$_{42/40}$ ratio relative to controls in both individuals with early and late onset depression were found, suggesting that age of onset might not influence plasma Aβ levels.

No relationship between levels of cognitive function, as measured by the MMSE, and plasma Aβ$_{42}$ levels was found. However, the MMSE alone may not be sensitive to the subtle cognitive abnormalities that may be present in depression and which may be associated with elevated plasma Aβ$_{42}$ levels. For example, there is evidence linking executive dysfunction to structural and functional brain abnormalities, including white matter pathology in depressed elderly (Alexopoulos, G. S. (2003), Role of executive function in late-life depression. *J Clin Psychiatry* 64 Suppl 14:18-23), which we found to be associated with increased Aβ$_{42/40}$ ratio.

Similarly, this study showed that treatment with either paroxetine or nortriptyline did not affect plasma Aβ levels. To the extent that elevation in Abeta$_{1-42}$ plays a major role in the development of a depressive disorder and/or depressive symptoms, which is the basis for the present invention, the failure of currently FDA approved medications to influence Abeta levels highlights an important limitation of current treatments. It is well known that greater than 30% of depressed patients do not respond to current FDA approved medications. It is also known that a significant number of those that do respond still experience residual depressive symptoms. Furthermore, it is also known that some patients relapse while under treatment with the FDA approved medications. Therefore, there is an unmet need for other therapies for this patient population.

We also found no significant relationship between indices of platelet activation (PF4 and β-TG) and plasma Aβ levels. This finding is consistent with a recent result of an in vitro study in which platelet activation produced no significant increase in either plasma Aβ$_{40}$ or Aβ$_{42}$ (Olsson, A., Vanmechelen, E., Vanderstichele, H., Davidsson, P., and Blennow, K. (2003), Unaltered plasma levels of beta-amyloid$_{(1-40)}$ and beta-amyloid$_{(1-42)}$ upon stimulation of human platelets. *Dement Geriatr Cogn Disord* 16:93-97), suggesting that other factors might have contributed to the elevated plasma Aβ$_{42}$ levels in depressed elderly. While platelet activation is believed to be a major source of peripheral Aβ, especially Aβ$_{40}$ (Chen, M., Inestrosa, N. C., Ross, G. S., and Fernandez, H. L. (1995), Platelets are the primary source of amyloid beta-peptide in human blood. *Biochem Biophys Res Commun* 213: 96-103-19; Li, Q. X., Berndt, M. C., Bush, A. I., Rumble, B., Mackenzie, I., Friedhuber, A., Beyreuther, K., and Masters, C. L. (1994), Membrane-associated forms of the bA4 amyloid protein precursor of Alzheimer's disease in human platelet and brain: Surface expression on the activated human platelet. *Blood* 84:133-142), APP is expressed in cells throughout the body and thus, these other sources might have contributed to plasma Aβ levels. There is emerging evidence that plasma and brain levels of soluble Aβ are in dynamic equilibrium with active receptor-mediated bidirectional transport across the blood brain barrier (BBB; 40), raising the possibility that the elevated plasma Aβ$_{42}$ that we observed in individuals with LLMD could reflect increased Aβ$_{42}$ levels in the brain.

The emergence of in vivo PET imaging techniques using specific ligands that bind to brain Aβ (Kung, M., Skovronsky, D. M., Hou, C., Zhuang, Z., Gur, T. L., Shang, B., Trojanowski, J. Q., Lee, V. M. Y., and Kung H F (2003), Detection of amyloid plaques by radioligands for Aβ$_{40}$ and Aβ$_{42}$. *J Mol Neurosci* 20:15-23) should allow the determination of whether brain Aβ levels are elevated in elderly depressives and whether these levels are related to plasma Aβ. Subsequent to our findings, Meltzer, C. et al. (Meltzer, C. et al., International Conference on Prevention of Dementia, Washington, D.C., Jul. 18-21, 2005) have recently provided in vivo evidence using the PET imaging technique that amyloid beta levels are elevated in the brains of non-demented, elderly individuals with late onset major depression. This finding complements our results of elevated plasma Abeta$_{42}$ in this population. Taken together, these findings are consistent with a generalized disturbance in Abeta metabolism in this patient population. However, a major limitation of these neuroimaging techniques at the present time is that they appear to detect only the Aβ that has been deposited in plaques and in the walls of small cerebral vessels and do not allow for the detection of oligomeric forms of these peptides or for the differentiation of Aβ$_{40}$ and Aβ$_{42}$ deposits. Therefore, they might not be sensitive to subtle and selective elevations in soluble Aβ$_{42}$ levels, suggested by our preliminary findings, which may be present long before the formation of the aggregated forms of these peptides detected by these techniques.

In summary, the study presented here shows elevations in plasma Aβ$_{42}$ and the Aβ$_{42/40}$ ratio and a significant correlation between the Aβ$_{42/40}$ ratio and severity of white matter hyperintensities in elderly individuals with LLMD. Abeta$_{1-42}$ may exhibit neurotoxicity and cause neurotransmitter alterations leading to depressive disorders and/or depressive symptoms. Therefore, based on the studies presented here, new therapies for depressive disorders or for treating the symptoms associated with such disorders should target Abeta$_{1-42}$ levels.

TABLE I

Criteria for Major Depressive Episode

A. Five (or more) of the following symptoms have been present during the same 2-week period and represent a change from previous functioning at least one of the symptoms is either (1) depressed mood or (2) loss of interest or pleasure. Note: Do not include symptoms that are clearly due to a general medical condition, or mood-incongruent delusions or hallucinations.
  (1) depressed mood most of the day, nearly every day, as indicated by either subjective report (e.g., feels sad or empty) or observation made by others (e.g., appears tearful). Note: In children and adolescents, can be irritable mood.
  (2) markedly diminished interest or pleasure in all, or almost all, activities most of the day, nearly every day (as indicated by either subjective account or observation made by others)
  (3) significant weight loss when not dieting or weight gain (e.g., a change of more than 5% of body weight in a month), or decrease or increase in appetite nearly every day. Note: In children, consider failure to make expected weight gains.
  (4) insomnia or hypersomnia nearly every day.
  (5) psychomotor agitation or retardation nearly every day (observable by others, not merely subjective feelings or restlessness or being slowed down).
  (6) fatigue or loss of energy nearly every day.
  (7) feelings of worthlessness or excessive or inappropriate guild (which may be delusional) nearly every day (not merely self-reproach or guilt about being sick).

TABLE I-continued

Criteria for Major Depressive Episode (8) diminished ability to think or concentrate, or indecisiveness, nearly every day (either by subjective account or as observed by others).
(9) recurrent thoughts of death (not just fear of dying), recurrent suicidal ideation without a specific plan, or a suicide attempt or a specific plan for committing suicide.
B. The symptoms do not meet criteria for a Mixed Depressive Episode.
C. The symptoms cause clinically significant distress or impairment in social, occupational, or other important areas of functioning.
D. The symptoms are not due to the direct physiological effects of a substance (e.g., a drug of abuse, a medication) or a general medical condition (e.g., hypothyroidism).
E. The symptoms are not better accounted for by Bereavement, i.e. after the loss of a loved one, the symptoms persist for longer than 2 months or are characterized by marked functional impairment, morbid preoccupation with worthlessness, suicidal ieation, psychotic symptoms, or psychomotor retardation.

TABLE II

Diagnostic criteria for 296.2x Major Depressive Disorder, Single Episode

A. Presence of a single Major Depressive Episode.
B. The Major Depressive Episode is not better accounted for by Schizoaffective Disorder and is not superimposed on Schizophrenia, Schizophreniform, Disorder, Delusional Disorder, or Psychotic Disorder not otherwise specified.
C. There has never been a Manic Episode, a Mixed Episode, or a Hypomanic Episode. Note: This exclusion does not apply if all of the manic-like, or hpyomanic-like episodes are substance or treatment induced or are due to the direct physiological effects of a general medical condition.

TABLE III

Diagnostic Criteria for 296.3x Major Depressive Disorder, Recurrent

A. Presence of two or more Major Depressive Episodes
Note: To be considered separate episodes, there must be an interval of at least 2 consecutive months in which criteria are not met for a Major Depressive Episode.
B. The Major Depressive Episodes are not better accounted for by Schizoaffective Disorder and are not superimposed on Schizophrenia, Schizophreniform Disorder, Delusional Disorder, or Psychotic Disorder not otherwise specified.
C. There has never been a manic episode, a Mixed Episode, or a Hypomanic Episode. Note: This exclusion does not apply if all of the manic-like, mixed-like, or hypomanic-like episodes are substance or treatment induced or are due to the direct physiological effects of a general medical condition.

What is claimed is:

1. A method of diagnosing major depression in an elderly subject not suffering from dementia comprising:
    a) collecting a biological test sample selected from the group consisting of whole blood, serum, and plasma from said subject;
    b) determining the level of amyloid beta present in the biological test sample;
    c) comparing the level of amyloid beta in the test sample with the level of amyloid beta in one or more persons free from major depression, or with a previously determined reference range for amyloid beta established from subjects free of major depression, and
    d) diagnosing major depression in the subject if the level of amyloid beta is higher in the biological test sample from the subject than the level of amyloid beta in one or more persons free from major depression, or with a previously determined reference range for amyloid beta established from subjects free of major depression.

2. The method of claim 1, wherein said amyloid beta is $A\beta_{40}$ or $A\beta_{42}$.

3. The method of claim 1, wherein the measurement of amyloid β comprises a quantitative method selected from the group consisting of an immunological or biochemical assay specific for amyloid β.

4. The method of claim 3, wherein said method is selected from the group consisting of an enzyme-linked immunosorbent assay (ELISA), and a Western blot assay.

5. The method of claim 3, wherein the quantitative method comprises
    a) contacting the test sample with an antibody that is immunospecific for amyloid beta; and
    b) quantitatively measuring any binding that has occurred between the antibody and the test sample.

6. The method of claim 5, wherein the antibody is a monoclonal or polyclonal antibody.

7. The method of claim 5, wherein the step of quantitatively measuring comprises testing a test sample with a plurality of antibodies for the quantitative detection of amyloid β.

* * * * *

```
                        SEQUENCE LISTING

<160> NUMBER OF SEQ ID NOS: 8

<210> SEQ ID NO 1
<211> LENGTH: 3416
<212> TYPE: DNA
<213> ORGANISM: Homo sapiens

<400> SEQUENCE: 1
gctgactcgc ctggctctga gccccgccgc cgcgctcggg ctccgtcagt ttcctcggca      60
gcggtaggcg agagcacgcg gaggagcgtg cgcgggggcc ccgggagacg gcggcggtgg     120
cggcgcgggc agagcaagga cgcggcggat cccactcgca cagcagcgca ctcggtgccc     180
cgcgcagggt cgcgatgctg cccggtttgg cactgctcct gctggccgcc tggacggctc     240
gggcgctgga ggtacccact gatggtaatg ctggcctgct ggctgaaccc cagattgcca     300
tgttctgtgg cagactgaac atgcacatga atgtccagaa tgggaagtgg gattcagatc     360
catcagggac caaaacctgc attgatacca aggaaggcat cctgcagtat tgccaagaag     420
tctaccctga actgcagatc accaatgtgg tagaagccaa ccaaccagtg accatccaga     480
actggtgcaa gcggggccgc aagcagtgca gacccatcc ccactttgtg attccctacc     540
gctgcttagt tggtgagttt gtaagtgatg cccttctcgt tcctgacaag tgcaaattct     600
tacaccagga gaggatggat gtttgcgaaa ctcatcttca ctggcacacc gtcgccaaag     660
agacatgcag tgagaagagt accaacttgc atgactacgg catgttgctg ccctgcggaa     720
ttgacaagtt ccgaggggta gagtttgtgt gttgcccact ggctgaagaa agtgacaatg     780
tggattctgc tgatgcggag gaggatgact cggatgtctg gtggggcgga gcagacacag     840
```

| | |
|---|---|
| actatgcaga tgggagtgaa gacaaagtag tagaagtagc agaggaggaa gaagtggctg | 900 |
| aggtggaaga agaagaagcc gatgatgacg aggacgatga ggatggtgat gaggtagagg | 960 |
| aagaggctga ggaaccctac gaagaagcca cagagagaac caccagcatt gccaccacca | 1020 |
| ccaccaccac cacagagtct gtggaagagg tggttcgagt tcctacaaca gcagccagta | 1080 |
| cccctgatgc cgttgacaag tatctcgaga cacctgggga tgagaatgaa catgcccatt | 1140 |
| tccagaaagc caaagagagg cttgaggcca agcaccgaga gagaatgtcc caggtcatga | 1200 |
| gagaatggga agaggcagaa cgtcaagcaa agaacttgcc taaagctgat aagaaggcag | 1260 |
| ttatccagca tttccaggag aaagtggaat ctttggaaca ggaagcagcc aacgagagac | 1320 |
| agcagctggt ggagacacac atggccagag tggaagccat gctcaatgac cgccgccgcc | 1380 |
| tggccctgga gaactacatc accgctctgc aggctgttcc tcctcggcct cgtcacgtgt | 1440 |
| tcaatatgct aaagaagtat gtccgcgcag aacagaagga cagacagcac accctaaagc | 1500 |
| atttcgagca tgtgcgcatg gtggatccca agaaagccgc tcagatccgg tcccaggtta | 1560 |
| tgacacacct ccgtgtgatt tatgagcgca tgaatcagtc tctctccctg ctctacaacg | 1620 |
| tgcctgcagt ggccgaggag attcaggatg aagttgatga gctgcttcag aaagagcaaa | 1680 |
| actattcaga tgacgtcttg gccaacatga ttagtgaacc aaggatcagt tacggaaacg | 1740 |
| atgctctcat gccatctttg accgaaacga aaaccaccgt ggagctcctt cccgtgaatg | 1800 |
| gagagttcag cctggacgat ctccagccgt ggcattcttt tggggctgac tctgtgccag | 1860 |
| ccaacacaga aaacgaagtt gagcctgttg atgcccgccc tgctgccgac cgaggactga | 1920 |
| ccactcgacc aggttctggg ttgacaaata tcaagacgga ggagatctct gaagtgaaga | 1980 |
| tggatgcaga attccgacat gactcaggat atgaagttca tcatcaaaaa ttggtgttct | 2040 |
| ttgcagaaga tgtgggttca aacaaaggtg caatcattgg actcatggtg ggcggtgttg | 2100 |
| tcatagcgac agtgatcgtc atcaccttgg tgatgctgaa gagaaacag tacacatcca | 2160 |
| ttcatcatgg tgtggtggag gttgacgccg ctgtcacccc agaggagcgc cacctgtcca | 2220 |
| agatgcagca gaacggctac gaaaatccaa cctacaagtt ctttgagcag atgcagaact | 2280 |
| agaccccccgc cacagcagcc tctgaagttg gacagcaaaa ccattgcttc actacccatc | 2340 |
| ggtgtccatt tatagaataa tgtgggaaga aacaaacccg ttttatgatt tactcattat | 2400 |
| cgccttttga cagctgtgct gtaacacaag tagatgcctg aacttgaatt aatccacaca | 2460 |
| tcagtaatgt attctatctc tctttacatt ttggtctcta tactacatta ttaatgggtt | 2520 |
| ttgtgtactg taaagaattt agctgtatca aactagtgca tgaatagatt ctctcctgat | 2580 |
| tatttatcac atagccccctt agccagttgt atattattct tgtggtttgt gacccaatta | 2640 |
| agtcctactt tacatatgct ttaagaatcg atgggggatg cttcatgtga acgtgggagt | 2700 |
| tcagctgctt ctcttgccta agtattcctt tcctgatcac tatgcatttt aaagttaaac | 2760 |
| attttttaagt atttcagatg cttttagagag attttttttc catgactgca ttttactgta | 2820 |
| cagattgctg cttctgctat atttgtgata taggaattaa aggatacac acgtttgttt | 2880 |
| cttcgtgcct gttttatgtg cacacattag gcattgagac ttcaagcttt tcttttttg | 2940 |
| tccacgtatc tttgggtctt tgataaagaa aagaatccct gttcattgta agcactttta | 3000 |
| cggggcgggg ggggagggggt gctctgctgg tcttcaatta ccaagaattc tccaaaacaa | 3060 |
| ttttctgcag gatgattgta cagaatcatt gcttatgaca tgatcgcttt ctacactgta | 3120 |
| ttacataaat aaattaaata aaataacccc gggcaagact tttctttgaa ggatgactac | 3180 |
| agacattaaa taatcgaagt aattttgggt ggggagaaga ggcagattca atttttctttta | 3240 |

```
accagtctga agtttcattt atgatacaaa agaagatgaa aatggaagtg gcaatataag    3300
gggatgagga aggcatgcct ggacaaaccc ttcttttaag atgtgtcttc aatttgtata    3360
aaatggtgtt ttcatgtaaa taaatacatt cttggaggag caaaaaaaaa aaaaaa       3416

<210> SEQ ID NO 2
<211> LENGTH: 120
<212> TYPE: DNA
<213> ORGANISM: Homo sapiens

<400> SEQUENCE: 2
gatgcagaat tccgacatga ctcaggatat gaagttcatc atcaaaaatt ggtgttcttt    60
gcagaagatg tgggttcaaa caaaggtgca atcattggac tcatggtggg cggtgttgtc   120

<210> SEQ ID NO 3
<211> LENGTH: 40
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 4
<211> LENGTH: 126
<212> TYPE: DNA
<213> ORGANISM: Homo sapiens

<400> SEQUENCE: 4
gatgcagaat tccgacatga ctcaggatat gaagttcatc atcaaaaatt ggtgttcttt    60
gcagaagatg tgggttcaaa caaaggtgca atcattggac tcatggtggg cggtgttgtc   120
atagcg                                                              126

<210> SEQ ID NO 5
<211> LENGTH: 42
<212> TYPE: PRT
<213> ORGANISM: Homo sapiens

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 6
<211> LENGTH: 7
<212> TYPE: PRT
<213> ORGANISM: Artificial Sequence
<220> FEATURE:
<221> NAME/KEY: Xaa
<222> LOCATION: (2)...(2)
<223> OTHER INFORMATION: Xaa is methylated leucine
<221> NAME/KEY: Xaa
<222> LOCATION: (4)...(4)
<223> OTHER INFORMATION: Xaa is methylated phenylalanine
```

-continued

```
<221> NAME/KEY: Xaa
<222> LOCATION: (6)...(6)
<223> OTHER INFORMATION: Xaa is methylated alanine
<223> OTHER INFORMATION: synthetic

<400> SEQUENCE: 6

Lys Leu Val Phe Phe Ala Glu
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic

<400> SEQUENCE: 7

Lys Leu Val Phe Phe
1               5

<210> SEQ ID NO 8
<211> LENGTH: 42
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```